(12) United States Patent
Sorgenfrei et al.

(10) Patent No.: US 12,138,068 B2
(45) Date of Patent: Nov. 12, 2024

(54) TECHNIQUES FOR CHARACTERIZING A NONLINEARITY OF A TIME-TO-DIGITAL CONVERTER IN AN OPTICAL MEASUREMENT SYSTEM

(71) Applicant: HI LLC, Los Angeles, CA (US)

(72) Inventors: Sebastian Sorgenfrei, Playa Vista, CA (US); Viswanath Ambalapuzha Gopalakrishnan, Culver City, CA (US); Katherine Perdue, Los Angeles, CA (US); Isai Olvera, San Jose, CA (US); Ryan Field, Culver City, CA (US)

(73) Assignee: HI LLC, Culver City, CA (US)

( * ) Notice: Subject to any disclaimer, the term of this patent is extended or adjusted under 35 U.S.C. 154(b) by 880 days.

(21) Appl. No.: 17/202,588

(22) Filed: Mar. 16, 2021

(65) Prior Publication Data

US 2021/0290146 A1 Sep. 23, 2021

Related U.S. Application Data

(60) Provisional application No. 63/059,382, filed on Jul. 31, 2020, provisional application No. 62/992,502, filed on Mar. 20, 2020.

(51) Int. Cl.
*G04F 10/00* (2006.01)
*A61B 5/00* (2006.01)
(Continued)

(52) U.S. Cl.
CPC .......... *A61B 5/4064* (2013.01); *A61B 5/0261* (2013.01); *A61B 5/7225* (2013.01);
(Continued)

(58) Field of Classification Search
CPC ................ A61B 5/4064; A61B 5/0059; A61B 5/0062; A61B 5/0066; A61B 5/0068;
(Continued)

(56) References Cited

U.S. PATENT DOCUMENTS

| 4,018,534 A | 4/1977 | Thorn et al. |
| 4,207,892 A | 6/1980 | Binder |

(Continued)

FOREIGN PATENT DOCUMENTS

| CN | 200950235 | 9/2007 |
| CN | 107865635 | 4/2018 |

(Continued)

OTHER PUBLICATIONS

International Search Report and Written Opinion received in International Application No. PCT/2020/027537, dated Sep. 7, 2020.

(Continued)

*Primary Examiner* — Lisa M Caputo
*Assistant Examiner* — Eric Sebastian Von Wald
(74) *Attorney, Agent, or Firm* — ALG Intellectual Property, LLC

(57) ABSTRACT

An illustrative optical measurement system includes a signal generator configured to generate a signal and a processing unit configured to direct the signal generator to apply the signal to a TDC included in the optical measurement system and generate, based on timestamp symbols recorded by the TDC in response to the signal, characterization data representative of a nonlinearity of the TDC.

18 Claims, 25 Drawing Sheets

(51) Int. Cl.
*A61B 5/026* (2006.01)
*G01J 1/44* (2006.01)
*H03M 1/50* (2006.01)

(52) U.S. Cl.
CPC .............. *G04F 10/005* (2013.01); *G01J 1/44* (2013.01); *H03M 1/50* (2013.01)

(58) Field of Classification Search
CPC ... A61B 5/0075; A61B 5/0082; A61B 5/0084; A61B 5/0086; A61B 5/0093; A61B 5/0095; A61B 5/486; A61B 5/7225; A61B 5/72; A61B 5/6803; A61B 2562/0238; A61B 2560/0443; A61B 2562/046; A61B 2560/0214; A61B 2560/0223; A61B 2576/026; A61B 5/0073; A61B 5/0042; G06F 3/015; G06K 7/10732; G06K 7/10851; G01J 1/4204; G01J 2001/442; G01J 1/0422; G01R 31/31725; G01R 31/31922; G01S 7/4863; G01S 17/10; G01S 17/18; G01S 7/4815; G01S 7/4865; G02B 27/0172; H03L 7/0805; H03L 7/0891; H03L 7/099; H03L 7/197; H03L 7/0996

See application file for complete search history.

(56) References Cited

U.S. PATENT DOCUMENTS

| | | |
|---|---|---|
| 4,281,645 A | 8/1981 | Jobsis |
| 4,321,930 A | 3/1982 | Jobsis |
| 4,515,165 A | 5/1985 | Carroll |
| 4,655,225 A | 4/1987 | Dahne et al. |
| 4,928,248 A | 5/1990 | Takahashi et al. |
| 4,963,727 A | 10/1990 | Cova |
| 4,995,044 A | 2/1991 | Blazo |
| 5,088,493 A | 2/1992 | Giannini |
| 5,090,415 A | 2/1992 | Yamashita |
| 5,218,962 A | 6/1993 | Mannheimer et al. |
| 5,309,458 A | 5/1994 | Carl |
| 5,386,827 A | 2/1995 | Chance et al. |
| 5,528,365 A | 6/1996 | Gonatas et al. |
| 5,625,458 A | 4/1997 | Alfano et al. |
| 5,761,230 A | 6/1998 | Oono et al. |
| 5,853,370 A | 12/1998 | Chance et al. |
| 5,895,984 A | 4/1999 | Renz |
| 5,924,982 A | 7/1999 | Chin |
| 5,929,982 A | 7/1999 | Anderson |
| 5,983,120 A | 11/1999 | Groner et al. |
| 5,987,045 A | 11/1999 | Albares et al. |
| 6,163,715 A | 12/2000 | Larsen et al. |
| 6,195,580 B1 | 2/2001 | Grable |
| 6,240,309 B1 | 5/2001 | Yamashita et al. |
| 6,291,824 B1 | 9/2001 | Battarbee et al. |
| 6,291,842 B1 | 9/2001 | Nakayama |
| 6,384,663 B2 | 5/2002 | Cova et al. |
| 6,541,752 B2 | 4/2003 | Zappa et al. |
| 6,542,763 B1 | 4/2003 | Yamashita et al. |
| 6,618,614 B1 | 9/2003 | Chance |
| 6,640,133 B2 | 10/2003 | Yamashita |
| 6,683,294 B1 | 1/2004 | Herbert et al. |
| 6,748,254 B2 | 6/2004 | O'Neil |
| 6,992,772 B2 | 1/2006 | Block |
| 7,095,491 B2 | 8/2006 | Forstner et al. |
| 7,356,365 B2 | 4/2008 | Schurman |
| 7,507,596 B2 | 3/2009 | Yaung et al. |
| 7,547,872 B2 | 6/2009 | Niclass et al. |
| 7,613,504 B2 | 11/2009 | Rowe |
| 7,667,400 B1 | 2/2010 | Goushcha |
| 7,705,284 B2 | 4/2010 | Inoue et al. |
| 7,714,292 B2 | 5/2010 | Agarwal et al. |
| 7,774,047 B2 | 8/2010 | Yamashita et al. |
| 7,888,973 B1* | 2/2011 | Rezzi ............... H03L 7/087 327/105 |
| 7,899,506 B2 | 3/2011 | Xu et al. |
| 8,026,471 B2 | 9/2011 | Itzler |
| 8,078,250 B2 | 12/2011 | Chen et al. |
| 8,082,015 B2 | 12/2011 | Yodh et al. |
| 8,115,170 B2 | 2/2012 | Stellari et al. |
| 8,168,934 B2 | 5/2012 | Niclass et al. |
| 8,269,563 B2* | 9/2012 | Ballantyne ............. H03L 7/099 331/34 |
| 8,352,012 B2 | 1/2013 | Besio |
| 8,633,431 B2 | 1/2014 | Kim |
| 8,637,875 B2 | 1/2014 | Finkelstein et al. |
| 8,754,378 B2 | 6/2014 | Prescher et al. |
| 8,817,257 B2 | 8/2014 | Herve |
| 8,937,509 B2 | 1/2015 | Xu et al. |
| 8,986,207 B2 | 3/2015 | Li |
| 9,012,860 B2 | 4/2015 | Nyman et al. |
| 9,041,136 B2 | 5/2015 | Chia |
| 9,058,081 B2 | 6/2015 | Baxter |
| 9,076,707 B2 | 7/2015 | Harmon |
| 9,101,279 B2 | 8/2015 | Ritchey et al. |
| 9,131,861 B2 | 9/2015 | Ince et al. |
| 9,157,858 B2 | 10/2015 | Claps |
| 9,160,949 B2 | 10/2015 | Zhang et al. |
| 9,176,241 B2 | 11/2015 | Frach |
| 9,178,100 B2 | 11/2015 | Webster et al. |
| 9,190,552 B2 | 11/2015 | Brunel et al. |
| 9,201,138 B2 | 12/2015 | Eisele et al. |
| 9,209,320 B1 | 12/2015 | Webster |
| 9,257,523 B2 | 2/2016 | Schneider et al. |
| 9,257,589 B2 | 2/2016 | Niclass et al. |
| 9,299,732 B2 | 3/2016 | Webster et al. |
| 9,299,873 B2 | 3/2016 | Mazzillo et al. |
| 9,312,401 B2 | 4/2016 | Webster |
| 9,316,735 B2 | 4/2016 | Baxter |
| 9,331,116 B2 | 5/2016 | Webster |
| 9,368,487 B1 | 6/2016 | Su et al. |
| 9,401,448 B2 | 7/2016 | Bienfang et al. |
| 9,407,796 B2 | 8/2016 | Dinten et al. |
| 9,419,635 B2 | 8/2016 | Kumar et al. |
| 9,431,439 B2 | 8/2016 | Soga et al. |
| 9,442,201 B2 | 9/2016 | Schmand et al. |
| 9,449,377 B2 | 9/2016 | Sarkar et al. |
| 9,450,007 B1 | 9/2016 | Motta et al. |
| 9,466,631 B2 | 10/2016 | Fallica et al. |
| 9,476,979 B2 | 10/2016 | Drader et al. |
| 9,478,579 B2 | 10/2016 | Dai et al. |
| 9,529,079 B1 | 12/2016 | Droz |
| 9,535,157 B2 | 1/2017 | Caley et al. |
| 9,554,738 B1* | 1/2017 | Gulati ................ A61B 5/0075 |
| 9,574,936 B2 | 2/2017 | Heinonen |
| 9,625,580 B2 | 4/2017 | Kotelnikov et al. |
| 9,627,569 B2 | 4/2017 | Harmon |
| 9,634,826 B1 | 4/2017 | Park |
| 9,639,063 B2 | 5/2017 | Dutton et al. |
| 9,640,704 B2 | 5/2017 | Frey et al. |
| 9,658,158 B2 | 5/2017 | Renna et al. |
| 9,659,980 B2 | 5/2017 | McGarvey et al. |
| 9,671,284 B1 | 6/2017 | Dandin |
| 9,681,844 B2 | 6/2017 | Xu et al. |
| 9,685,576 B2 | 6/2017 | Webster |
| 9,702,758 B2 | 7/2017 | Nouri |
| 9,728,659 B2 | 8/2017 | Hirigoyen et al. |
| 9,741,879 B2 | 8/2017 | Frey et al. |
| 9,753,351 B2 | 9/2017 | Eldada |
| 9,767,246 B2 | 9/2017 | Dolinsky et al. |
| 9,768,211 B2 | 9/2017 | Harmon |
| 9,773,930 B2 | 9/2017 | Motta et al. |
| 9,804,092 B2 | 10/2017 | Zeng et al. |
| 9,812,438 B2 | 11/2017 | Schneider et al. |
| 9,831,283 B2 | 11/2017 | Shepard et al. |
| 9,851,302 B2 | 12/2017 | Mattioli Della Rocca et al. |
| 9,867,250 B1 | 1/2018 | Powers et al. |
| 9,869,753 B2 | 1/2018 | Eldada |
| 9,881,963 B1 | 1/2018 | Chen et al. |
| 9,882,003 B1 | 1/2018 | Aharoni |
| 9,886,095 B2 | 2/2018 | Pothier |
| 9,899,544 B1 | 2/2018 | Mazzillo et al. |
| 9,899,557 B2 | 2/2018 | Muscara' et al. |
| 9,939,316 B2 | 4/2018 | Scott et al. |

(56) References Cited

U.S. PATENT DOCUMENTS

| | | | |
|---|---|---|---|
| 9,939,536 B2 | 4/2018 | O'Neill et al. |
| 9,946,344 B2 | 4/2018 | Ayaz et al. |
| D817,553 S | 5/2018 | Aaskov et al. |
| 9,983,670 B2 | 5/2018 | Coleman |
| 9,997,551 B2 | 6/2018 | Mandai et al. |
| 10,016,137 B1 | 7/2018 | Yang et al. |
| D825,112 S | 8/2018 | Saez |
| 10,056,415 B2 | 8/2018 | Na et al. |
| 10,103,513 B1 | 10/2018 | Zhang et al. |
| 10,141,458 B2 | 11/2018 | Zhang et al. |
| 10,154,815 B2 | 12/2018 | Al-Ali et al. |
| 10,157,954 B2 | 12/2018 | Na et al. |
| 10,158,038 B1 | 12/2018 | Do Valle et al. |
| 10,219,700 B1 | 3/2019 | Yang et al. |
| 10,256,264 B2 | 4/2019 | Na et al. |
| 10,340,408 B1 | 7/2019 | Katnani |
| 10,424,683 B1 | 9/2019 | Do Valle |
| 10,483,125 B2 | 11/2019 | Inoue |
| 10,515,993 B2 | 12/2019 | Field et al. |
| 10,533,893 B2 | 1/2020 | Leonardo |
| 10,541,660 B2 | 1/2020 | McKisson |
| 10,558,171 B2 | 2/2020 | Kondo |
| 10,594,306 B2 | 3/2020 | Dandin |
| 10,627,460 B2 | 4/2020 | Alford et al. |
| 10,695,167 B2 | 6/2020 | Van Heugten et al. |
| 10,697,829 B2 | 6/2020 | Delic |
| 10,772,561 B2 | 9/2020 | Donaldson |
| 10,809,796 B2 | 10/2020 | Armstrong-Muntner |
| 10,825,847 B2 | 11/2020 | Furukawa |
| 10,912,504 B2 | 2/2021 | Nakaji |
| 10,976,386 B2 | 4/2021 | Alford |
| 10,983,177 B2 | 4/2021 | Jiménez-Martínez |
| 10,996,293 B2 | 5/2021 | Mohseni |
| 11,006,876 B2 | 5/2021 | Johnson |
| 11,006,878 B2 | 5/2021 | Johnson |
| 11,137,283 B2 | 10/2021 | Balamurugan et al. |
| 11,213,245 B2 | 1/2022 | Horstmeyer et al. |
| 11,630,310 B2 | 4/2023 | Seidman et al. |
| 2002/0033454 A1 | 3/2002 | Cheng et al. |
| 2002/0195545 A1 | 12/2002 | Nishimura |
| 2004/0057478 A1 | 3/2004 | Saito |
| 2004/0064052 A1 | 4/2004 | Chance et al. |
| 2004/0078216 A1 | 4/2004 | Toto |
| 2004/0160996 A1 | 8/2004 | Giorgi et al. |
| 2005/0038344 A1 | 2/2005 | Chance |
| 2005/0059869 A1 | 3/2005 | Scharf et al. |
| 2005/0061986 A1 | 3/2005 | Kardynal et al. |
| 2005/0124863 A1 | 6/2005 | Cook |
| 2005/0228291 A1 | 10/2005 | Chance |
| 2006/0171845 A1 | 8/2006 | Martin |
| 2006/0197452 A1 | 9/2006 | Zhang |
| 2006/0264722 A1 | 11/2006 | Hannula et al. |
| 2007/0038116 A1 | 2/2007 | Yamanaka |
| 2007/0083097 A1 | 4/2007 | Fujiwara |
| 2008/0021341 A1 | 1/2008 | Harris et al. |
| 2009/0012402 A1 | 1/2009 | Mintz |
| 2009/0054789 A1 | 2/2009 | Kiguchi et al. |
| 2009/0163775 A1 | 6/2009 | Barrett |
| 2009/0313048 A1 | 12/2009 | Kahn et al. |
| 2010/0007413 A1 | 1/2010 | Herleikson et al. |
| 2010/0188649 A1 | 7/2010 | Prahl et al. |
| 2010/0210952 A1 | 8/2010 | Taira et al. |
| 2010/0249557 A1 | 9/2010 | Besko et al. |
| 2010/0301194 A1 | 12/2010 | Patel |
| 2011/0208675 A1 | 8/2011 | Shoureshi et al. |
| 2011/0248175 A1 | 10/2011 | Frach |
| 2012/0016635 A1 | 1/2012 | Brodsky et al. |
| 2012/0029304 A1 | 2/2012 | Medina et al. |
| 2012/0083673 A1 | 4/2012 | Al-Ali et al. |
| 2012/0101838 A1 | 4/2012 | Lingard et al. |
| 2013/0015331 A1 | 1/2013 | Birk |
| 2013/0030267 A1 | 1/2013 | Lisogurski |
| 2013/0030270 A1 | 1/2013 | Chiou et al. |
| 2013/0032713 A1 | 2/2013 | Barbi et al. |
| 2013/0090541 A1 | 4/2013 | Macfarlane et al. |
| 2013/0144644 A1 | 6/2013 | Simpson |
| 2013/0153754 A1 | 6/2013 | Drader et al. |
| 2013/0221221 A1 | 8/2013 | Bouzid et al. |
| 2013/0225953 A1 | 8/2013 | Oliviero et al. |
| 2013/0300838 A1* | 11/2013 | Borowski ............ G01S 7/4863 348/46 |
| 2013/0342835 A1 | 12/2013 | Blacksberg |
| 2014/0027607 A1 | 1/2014 | Mordarski et al. |
| 2014/0028211 A1 | 1/2014 | Imam |
| 2014/0055181 A1 | 2/2014 | Chavpas |
| 2014/0066783 A1 | 3/2014 | Kiani |
| 2014/0171757 A1 | 6/2014 | Kawato et al. |
| 2014/0185643 A1 | 7/2014 | McComb et al. |
| 2014/0191115 A1 | 7/2014 | Webster et al. |
| 2014/0211194 A1 | 7/2014 | Pacala et al. |
| 2014/0217264 A1 | 8/2014 | Shepard |
| 2014/0275891 A1 | 9/2014 | Muehlemann et al. |
| 2014/0289001 A1 | 9/2014 | Shelton |
| 2014/0291481 A1 | 10/2014 | Zhang et al. |
| 2015/0011848 A1 | 1/2015 | Ruchti et al. |
| 2015/0038811 A1 | 2/2015 | Asaka |
| 2015/0038812 A1 | 2/2015 | Ayaz et al. |
| 2015/0041625 A1 | 2/2015 | Dutton |
| 2015/0041627 A1 | 2/2015 | Webster |
| 2015/0054111 A1 | 2/2015 | Niclass et al. |
| 2015/0057511 A1 | 2/2015 | Basu |
| 2015/0077279 A1 | 3/2015 | Song |
| 2015/0094552 A1 | 4/2015 | Golda |
| 2015/0150505 A1 | 6/2015 | Kaskoun et al. |
| 2015/0157262 A1 | 6/2015 | Schuessler |
| 2015/0157435 A1 | 6/2015 | Chasins et al. |
| 2015/0182136 A1 | 7/2015 | Durduran et al. |
| 2015/0192677 A1 | 7/2015 | Yu et al. |
| 2015/0200222 A1 | 7/2015 | Webster |
| 2015/0201841 A1 | 7/2015 | Ishikawa et al. |
| 2015/0293224 A1 | 10/2015 | Eldada et al. |
| 2015/0327777 A1 | 11/2015 | Kostic et al. |
| 2015/0333095 A1 | 11/2015 | Fallica et al. |
| 2015/0355019 A1 | 12/2015 | Nouri et al. |
| 2015/0364635 A1 | 12/2015 | Bodlovic et al. |
| 2016/0049765 A1 | 2/2016 | Eldada |
| 2016/0057369 A1 | 2/2016 | Wolfe et al. |
| 2016/0099371 A1 | 4/2016 | Webster |
| 2016/0119983 A1 | 4/2016 | Moore |
| 2016/0150963 A1 | 6/2016 | Roukes et al. |
| 2016/0161600 A1 | 6/2016 | Eldada et al. |
| 2016/0181302 A1 | 6/2016 | McGarvey et al. |
| 2016/0182902 A1 | 6/2016 | Guo |
| 2016/0218236 A1 | 7/2016 | Dhulla et al. |
| 2016/0247301 A1 | 8/2016 | Fang |
| 2016/0278715 A1 | 9/2016 | Yu et al. |
| 2016/0287107 A1 | 10/2016 | Szabados |
| 2016/0296168 A1 | 10/2016 | Abreu |
| 2016/0341656 A1 | 11/2016 | Liu et al. |
| 2016/0345880 A1 | 12/2016 | Nakaji et al. |
| 2016/0349368 A1* | 12/2016 | Stutz ..................... G04F 10/10 |
| 2016/0356718 A1 | 12/2016 | Yoon et al. |
| 2016/0357260 A1 | 12/2016 | Raynor et al. |
| 2017/0030769 A1 | 2/2017 | Clemens et al. |
| 2017/0047372 A1 | 2/2017 | McGarvey et al. |
| 2017/0052065 A1 | 2/2017 | Sharma et al. |
| 2017/0085547 A1 | 3/2017 | De Aguiar et al. |
| 2017/0118423 A1 | 4/2017 | Zhou et al. |
| 2017/0124713 A1 | 5/2017 | Jurgenson et al. |
| 2017/0131143 A1 | 5/2017 | Andreou et al. |
| 2017/0139041 A1 | 5/2017 | Drader et al. |
| 2017/0141100 A1 | 5/2017 | Tseng et al. |
| 2017/0164857 A1 | 6/2017 | Brugere |
| 2017/0172447 A1 | 6/2017 | Mitra et al. |
| 2017/0176579 A1 | 6/2017 | Niclass et al. |
| 2017/0176596 A1 | 6/2017 | Shpunt et al. |
| 2017/0179173 A1 | 6/2017 | Mandai et al. |
| 2017/0186798 A1 | 6/2017 | Yang et al. |
| 2017/0202518 A1 | 7/2017 | Furman et al. |
| 2017/0265822 A1 | 9/2017 | Du |
| 2017/0276545 A1 | 9/2017 | Henriksson |
| 2017/0281086 A1 | 10/2017 | Donaldson |
| 2017/0299700 A1 | 10/2017 | Pacala et al. |
| 2017/0303789 A1 | 10/2017 | Tichauer et al. |

(56) References Cited

U.S. PATENT DOCUMENTS

| | | |
|---|---|---|
| 2017/0314989 A1 | 11/2017 | Mazzillo et al. |
| 2017/0338969 A1 | 11/2017 | Paul et al. |
| 2017/0363467 A1 | 12/2017 | Clemens et al. |
| 2017/0367650 A1 | 12/2017 | Wallois |
| 2018/0003821 A1 | 1/2018 | Imai |
| 2018/0014741 A1 | 1/2018 | Chou |
| 2018/0019268 A1 | 1/2018 | Zhang et al. |
| 2018/0020960 A1 | 1/2018 | Sarussi |
| 2018/0026147 A1 | 1/2018 | Zhang et al. |
| 2018/0027196 A1 | 1/2018 | Yang et al. |
| 2018/0033895 A1 | 2/2018 | Mazzillo et al. |
| 2018/0039053 A1 | 2/2018 | Kremer et al. |
| 2018/0045816 A1 | 2/2018 | Jarosinski et al. |
| 2018/0062345 A1 | 3/2018 | Bills et al. |
| 2018/0066986 A1 | 3/2018 | Kasai et al. |
| 2018/0069043 A1 | 3/2018 | Pan et al. |
| 2018/0070830 A1 | 3/2018 | Sutin et al. |
| 2018/0070831 A1 | 3/2018 | Sutin et al. |
| 2018/0081061 A1 | 3/2018 | Mandai et al. |
| 2018/0089531 A1 | 3/2018 | Geva et al. |
| 2018/0089848 A1 | 3/2018 | Yang et al. |
| 2018/0090526 A1 | 3/2018 | Mandai et al. |
| 2018/0090536 A1 | 3/2018 | Mandai et al. |
| 2018/0102442 A1 | 4/2018 | Wang et al. |
| 2018/0103528 A1 | 4/2018 | Moore |
| 2018/0103861 A1 | 4/2018 | Sutin et al. |
| 2018/0117331 A1 | 5/2018 | Kuzniecky |
| 2018/0120152 A1 | 5/2018 | Leonardo |
| 2018/0122560 A1 | 5/2018 | Okuda |
| 2018/0156660 A1 | 6/2018 | Turgeon |
| 2018/0167606 A1 | 6/2018 | Cazaux et al. |
| 2018/0175230 A1 | 6/2018 | Droz et al. |
| 2018/0180473 A1 | 6/2018 | Clemens et al. |
| 2018/0185667 A1 | 7/2018 | Huang |
| 2018/0192931 A1 | 7/2018 | Linden et al. |
| 2018/0217261 A1 | 8/2018 | Wang |
| 2018/0296094 A1 | 10/2018 | Nakamura |
| 2018/0366342 A1 | 12/2018 | Inque et al. |
| 2019/0006399 A1 | 1/2019 | Otake et al. |
| 2019/0025406 A1 | 1/2019 | Krelboim et al. |
| 2019/0026849 A1 | 1/2019 | Demeyer |
| 2019/0088697 A1 | 3/2019 | Furukawa et al. |
| 2019/0091483 A1 | 3/2019 | Deckert |
| 2019/0113385 A1 | 4/2019 | Fukuchi |
| 2019/0120975 A1 | 4/2019 | Ouvrier-Buffet |
| 2019/0167211 A1 | 6/2019 | Everman et al. |
| 2019/0175068 A1 | 6/2019 | Everdell |
| 2019/0192031 A1 | 6/2019 | Laszlo et al. |
| 2019/0200888 A1 | 7/2019 | Poltorak |
| 2019/0209012 A1 | 7/2019 | Yoshimoto et al. |
| 2019/0239753 A1 | 8/2019 | Wentz |
| 2019/0261869 A1 | 8/2019 | Franceschini |
| 2019/0298158 A1 | 10/2019 | Dhaliwal |
| 2019/0343395 A1 | 11/2019 | Cussac |
| 2019/0355773 A1 | 11/2019 | Field et al. |
| 2019/0355861 A1 | 11/2019 | Katnani |
| 2019/0363210 A1 | 11/2019 | Do Valle |
| 2019/0378869 A1 | 12/2019 | Field et al. |
| 2019/0388018 A1 | 12/2019 | Horstmeyer |
| 2019/0391213 A1 | 12/2019 | Alford |
| 2020/0022581 A1 | 1/2020 | Vanegas |
| 2020/0041727 A1 | 2/2020 | Yamamoto |
| 2020/0044098 A1 | 2/2020 | Azuma |
| 2020/0056263 A1 | 2/2020 | Bhattacharyya |
| 2020/0057115 A1 | 2/2020 | Jiménez-Martínez |
| 2020/0057116 A1 | 2/2020 | Zorzos et al. |
| 2020/0057146 A1 | 2/2020 | Steinkogler et al. |
| 2020/0060542 A1 | 2/2020 | Alford |
| 2020/0088811 A1 | 3/2020 | Mohseni |
| 2020/0109481 A1 | 4/2020 | Sobek |
| 2020/0123416 A1 | 4/2020 | Bhattacharyya |
| 2020/0136632 A1 | 4/2020 | Lin |
| 2020/0182692 A1 | 6/2020 | Lilic |
| 2020/0188030 A1 | 6/2020 | Kopper et al. |
| 2020/0191883 A1 | 6/2020 | Bhattacharyya |
| 2020/0196932 A1 | 6/2020 | Johnson et al. |
| 2020/0241094 A1 | 7/2020 | Alford |
| 2020/0253479 A1 | 8/2020 | Nurmikko |
| 2020/0256929 A1 | 8/2020 | Ledbetter et al. |
| 2020/0309873 A1 | 10/2020 | Ledbetter et al. |
| 2020/0315510 A1 | 10/2020 | Johnson |
| 2020/0334559 A1 | 10/2020 | Anderson |
| 2020/0337624 A1 | 10/2020 | Johnson |
| 2020/0341081 A1 | 10/2020 | Mohseni et al. |
| 2020/0348368 A1 | 11/2020 | Garber et al. |
| 2020/0379095 A1* | 12/2020 | Kappel .................. G01S 7/497 |
| 2020/0381128 A1 | 12/2020 | Pratt |
| 2020/0390358 A1 | 12/2020 | Johnson |
| 2020/0393902 A1 | 12/2020 | Mann et al. |
| 2020/0400763 A1 | 12/2020 | Pratt |
| 2021/0015385 A1 | 1/2021 | Katnani |
| 2021/0011094 A1 | 2/2021 | Bednarke |
| 2021/0041512 A1 | 2/2021 | Pratt |
| 2021/0063510 A1 | 3/2021 | Ledbetter |
| 2021/0013974 A1 | 5/2021 | Seidman |
| 2021/0139742 A1 | 5/2021 | Seidman |
| 2021/0186138 A1 | 6/2021 | Bartels et al. |
| 2021/0223098 A1 | 7/2021 | Ledvina et al. |
| 2021/0265512 A1 | 8/2021 | Ayel |
| 2021/0290064 A1 | 9/2021 | Do Valle |
| 2021/0294996 A1 | 9/2021 | Field |

FOREIGN PATENT DOCUMENTS

| | | |
|---|---|---|
| EP | 0656536 | 4/2004 |
| EP | 2294973 | 3/2011 |
| EP | 3419168 | 12/2018 |
| EP | 3487072 | 5/2019 |
| FR | 3011932 A1 | 4/2015 |
| JP | 2012125370 A | 1/2015 |
| KR | 20170087639 A | 7/2017 |
| WO | 8804034 | 6/1988 |
| WO | 1999053577 | 10/1999 |
| WO | 2008144831 | 12/2008 |
| WO | 2011083563 | 7/2011 |
| WO | 2012135068 | 10/2012 |
| WO | 2013034770 | 3/2013 |
| WO | 2013066959 | 5/2013 |
| WO | 2015052523 | 4/2015 |
| WO | 2015109005 | 7/2015 |
| WO | 2016166002 | 10/2016 |
| WO | 2017004663 | 1/2017 |
| WO | 2017083826 | 5/2017 |
| WO | 2017130682 | 8/2017 |
| WO | 2017150146 | 9/2017 |
| WO | 2017203936 | 11/2017 |
| WO | 2018007829 | 1/2018 |
| WO | 2018033751 | 2/2018 |
| WO | 2018122560 | 7/2018 |
| WO | 2019221784 | 11/2019 |

OTHER PUBLICATIONS

International Search Report and Written Opinion received in International Application No. PCT/2020/028820, dated Aug. 26, 2020.

International Search Report and Written Opinion received in International Application No. PCT/US20/34062, dated Aug. 26, 2020.

International Search Report and Written Opinion received in International Application No. PCT/US2018/058580, dated Feb. 12, 2019.

International Search Report and Written Opinion received in International Application No. PCT/US2018/062777, dated Feb. 13, 2019.

International Search Report and Written Opinion received in International Application No. PCT/US2019/019317, dated May 28, 2019.

Non-Final Office Action received in U.S. Appl. No. 16/177,351, dated Apr. 1, 2019.

Non-Final Office Action received in U.S. Appl. No. 16/283,730, dated May 16, 2019.

Non-Final Office Action received in U.S. Appl. No. 16/370,991, dated Feb. 10, 2020.

(56) References Cited

OTHER PUBLICATIONS

Non-Final Office Action received in U.S. Appl. No. 16/537,360, dated Feb. 25, 2020.
Non-Final Office Action received in U.S. Appl. No. 16/544,850, dated Jun. 25, 2020.
Non-Final Office Action received in U.S. Appl. No. 16/856,524, dated Dec. 1, 2020.
Partial Search Report received in International Application No. PCT/2020/028820, dated Jul. 1, 2020.
Partial Search Report received in International Application No. PCT/US2020/027537, dated Jul. 17, 2020.
Alayed, et al., "Characterization of a Time-Resolved Diffuse Optical Spectroscopy Prototype Using Low-Cost, Compact Single Photon Avalanche Detectors for Tissue Optics Applications," Sensors 2018, 18, 3680; doi:10.3390/s18113680, Oct. 29, 2018.
Bellis, et al., "Photon counting imaging: the DigitalAPD," Society of Photo-Optical Instrumentation Engineers (SPIE) Conference Series, Feb. 2006, vol. 6066, pp. 111-120.
Blutman, et al.,"A 0.1 pJ Freeze Vernier Time-to-Digital Converter in 65nm CMOS," 2014 International Symposium on Circuits and Systems (ISCAS), Melbourne, Australia, Jun. 1-5, 2014.
Cambie, et al.,"Every photon counts: understanding and optimizing photon paths in luminescent solar concentrator-based photomicroreactors (LSC-PMs)," React. Chem. Eng., 2017, 2, 561-566.
Contini, et al., "Photon migration through a turbid slab described by a model based on diffusion approximation. I. Theory," Appl. Opt. 36(19), 4587 (1997).
Dalla Mora, et al., "Fast-Gated Single-Photon Avalanche Diode for Wide Dynamic Range Near Infrared Spectroscopy," IEEE Journal of Selected Topics in Quantum Electronics, vol. 16, No. 4, Jul./Aug. 2010.
Dalla Mora, et al., "Memory effect in silicon time-gated single-photon avalanche diodes," http://dx.doi.org/10.1063/1.4915332, Journal of Applied Physics 117, 114501, 2015.
De Heyn, et al., "A fast start-up 3GHz-10GHz digitally controlled oscillator for UWB impulse radio in 90nm CMOS," 2007 European Solid-State Circuits Conference—(ESSCIRC), Munich, Germany, pp. 484-487, Sep. 11-13, 2007.
Di Sieno, et al., "Probe-hosted large area silicon photomultiplier and high-throughput timing electronics for enhanced performance time-domain functional near-infrared spectroscopy," Biomed. Opt. Express 11(11), 6389 (2020).
Doernberg, et al., "Full-Speed Testing of A/D Converters," IEEE Journal of Solid-State Circuits, vol. SC-19, No. 6, Dec. 1984.
Dutton, et al., "A Time-Correlated Single-Photon-Counting Sensor with 14GS/s Histogramming Time-to-Digital Converter," 2015 IEEE International Solid-State Circuits Conference ISSCC 2015 / Session 11 / Sensors and Imagers for Life Sciences / 11.5, Feb. 22-26, 2015.
Fishburn, et al., "Temporal Derivative Distribution Repair (TDDR): A motion correction method for fNIRS," Neuroimage. Jan. 1, 2019: 184: 171-179. doi:10.1016/j.neuroimage.2018.09.025.
Fisher, et al., "A Reconfigurable Single-Photon-Counting Integrating Receiver for Optical Communications," IEEE Journal of Solid-State Circuits, vol. 48, No. 7, Jul. 2013, https://www.researchgate.net/publication/260626902.
Gallivanoni, et al., "Progress in Quenching Circuits for Single Photon Avalanche Diodes," IEEE Transactions on Nuclear Science, vol. 57, No. 6, Dec. 2010.
Ginetti, et al., "Reliability of Code Density Test for High Resolution ADCs," Electronics Letters, Nov. 1991, vol. 27, No. 24.
Gnecchi, et al., "A 1×16 SIPM Array for Automotive 3D Imaging LIDAR Systems.", Proceedings of the 2017 International Image Sensor Workshop (IISW), Hiroshima, Japan (2017).
Harmon, et al., "Compound Semiconductor SPAD Arrays," LightSpin Technologies, http://www.lightspintech.com/publications.html (2013).
Henderson, et al., "A 192 × 128 Time Correlated SPAD Image Sensor in 40-nm CMOS Technology," IEEE Journal of Solid-State Circuits, 2019.
Henderson, et al., "A 256×256 40nm/90nm CMOS 3D-Stacked 120dB Dynamic-Range Reconfigurable Time-Resolved SPAD Imager," 2019 IEEE International Solid- State Circuits Conference—(ISSCC), San Francisco, CA, USA, 2019, pp. 106-108. doi: 10.1109/ISSCC.2019.8662355.
Huppert, et al., "HomER: a review of time-series analysis methods for near-infrared spectroscopy of the brain," Appl. Opt. 48(10), D280 (2009).
Kienle, et al., "Improved solutions of the steady-state and the time-resolved diffusion equations for reflectance from a semi-infinite turbid medium," J. Opt. Soc. Am. A 14(1), 246 (1997).
Konugolu, et al., "Broadband (600-1350 nm) Time-Resolved Diffuse Optical Spectrometer for Clinical Use," IEEE Journal of Selected Topics in Quantum Electronics, vol. 22, No. 3, May/Jun. 2016.
Lacerenza, et al., "Wearable and wireless time-domain near-infrared spectroscopy system for brain and muscle hemodynamic monitoring," Biomed. Opt. Express 11(10), 5934 (2020).
Lange, et al.,"Clinical Brain Monitoring with Time Domain NIRS: A Review and Future Perspectives," Applied Sciences 9(8), 1612 (2019).
Lange, et al.,"MAESTROS: A Multiwavelength Time-Domain NIRS System to Monitor Changes in Oxygenation and Oxidation State of Cytochrome-C-Oxidase," IEEE J. Select. Topics Quantum Electron. 25(1), 1-12 (2019).
Lee, et al., "High-Performance Back-Illuminated Three-Dimensional Stacked Single-Photon Avalanche Diode Implemented in 45-nm CMOS Technology," IEEE Journal of Selected Topics in Quantum Electronics 6, 1-9 (2018).
Mandai, et al., "A 4 × 4 × 416 digital SiPM array with 192 TDCs for multiple high-resolution timestamp acquisition," 2013 JINST 8 PO5024, May 31, 2013.
Martelli, et al.,"Optimal estimation reconstruction of the optical properties of a two-layered tissue phantom from time-resolved single-distance measurements," Journal of Biomedical Optics 20(11), 115001 (Nov. 2015).
Maruyama, et al., "A 1024 × 8, 700-ps Time-Gated SPAD Line Sensor for Planetary Surface Exploration With Laser Raman Spectroscopy and Libs," IEEE Journal of Solid-State Circuits, vol. 49, No. 1, Jan. 2014.
Mita, et al., "High-Speed and Compact Quenching Circuit for Single-Photon Avalanche Diodes," IEEE Transactions on Instrumentation and Measurement, vol. 57, No. 3, Mar. 2008. pp. 543-547.
Mora, et al., "Fast silicon photomultiplier improves signal harvesting and reduces complexity in time-domain diffuse optics," Opt. Express 23(11), 13937 (2015).
Mora, et al., "Fast-Gated Single-Photon Avalanche Diode for Wide Dynamic Range Near Infrared Spectroscopy," IEEE Journal of Selected Topics in Quantum Electronics, vol. 16, No. 4, pp. 1023-1030, Jul./Aug. 2010.
Parmesan, et al., "A 256 × 256 SPAD array with in-pixel Time to Amplitude Conversion for Fluorescence Lifetime Imaging Microscopy,", Memory 900.M4, 2015.
Pifferi, et al., "Performance assessment of photon migration instruments: the MEDPHOT protocol," Applied Optics, 44(11), 2104-2114 (2005).
Prahl, et al., "Optical Absorption of Hemoglobin," http://omlc.ogi.edu/spectra/hemoglobin/index.html (1999).
Puszka, et al., "Time-resolved diffuse optical tomography using fast-gated single-photon avalanche diodes," Biomedical optics express, 2013, vol. 4, No. 8, pp. 1351-1365 (Year: 2013).
Re, et al., "Multi-channel medical device for time domain functional near infrared spectroscopy based on wavelength space multiplexing," Biomed. Opt. Express 4(10), 2231 (2013).
Renna, et al., "Eight-Wavelength, Dual Detection Channel Instrument for Near-Infrared Time-Resolved Diffuse Optical Spectroscopy," IEEE J. Select. Topics Quantum Electron. 25(1), 1-11 (2019).
Richardson, et al.,"A 32×32 50ps resolution 10 bit time to digital converter array in 130nm CMOS for time correlated imaging," CICC 2009 Proceedings of the IEEE 2009 Custom Integrated Circuits Conference. IEEE Society, San Jose, U.S.A., pp. 77-80, CICC 2009, San Jose, U.S.A., Sep. 13, 2009. https://doi.org/doi:10.1109/CICC.2009.5280890.

(56) References Cited

OTHER PUBLICATIONS

Takai, et al., "Single-Photon Avalanche Diode with Enhanced NIR-Sensitivity for Automotive LIDAR Systems," Sensors, 2016, 16(4): 459, pp. 1-9 (Year: 2016).
Ting, et al., "A Histogram-Based Testing Method for Estimating A/D Converter Performance," IEEE Transactions on Instrumentation and Measurement, vol. 57, No. 2, Feb. 2008.
Torricelli, et al., "Time domain functional NIRS imaging for human brain mapping," NeuroImage 85, 28-50 (2014).
Wabnitz, et al., "Depth-selective data analysis for time-domain fNIRS: moments vs. time windows," Biomed. Opt. Express 11(8), 4224 (2020).
Wabnitz, et al., "Performance assessment of time-domain optical brain imagers, part 1: basic instrumental performance protocol," Journal of Biomedical Optics 19(8), 086010 (Aug. 2014).
Wabnitz, et al., "Performance assessment of time-domain optical brain imagers, part 2: nEUROPt protocol," Journal of Biomedical Optics 19(8), 086012 (Aug. 2014).
Wojtkiewicz, et al., "Self-calibrating time-resolved near infrared spectroscopy," Biomed. Opt. Express 10(5), 2657 (2019).
Zhang, et al., "A CMOS SPAD Imager with Collision Detection and 128 Dynamically Reallocating TDCs for Single-Photon Counting and 3D Time-of-Flight Imaging," Sensors (Basel, Switzerland), 18(11), 4016. doi:10.3390/s18114016 Nov. 17, 2018.
Zucchelli, et al., "Method for the discrimination of superficial and deep absorption variations by time domain fNIRS," 2013 OSA Dec. 1, 2013 | vol. 4, No. 12 | DOI:10.1364/BOE.4.002893 | Biomedical Optics Express 2893.
"emojipedia.org", https://emojipedia.org (accessed May 27, 2021).
"International Search Report and Written Opinion received in International Application No. PCT/2021/018188".
"International Search Report and Written Opinion received in International Application No. PCT/US2021/018155".
"International Search Report and Written Opinion received in International Application No. PCT/US2021/018187".
"International Search Report and Written Opinion received in International Application No. PCT/US2021/018190".
"scienceofpeople.com/emojis", https://www.scienceofpeople.com/emojis/ (accessed May 27, 2021).
Hebert, et al., "Spatiotemporal image correlation spectroscopy (STICS) theory, verification, and application to protein velocity mapping in living CHO cells", Biophysical journal 88, No. 5 (2005): 3601-3614.
Kheng, et al., "Image Processing", https://www.comp.nus.edu.sg/~cs4243/lecture/imageproc.pdf, Mar. 9, 2014.
Sneha, et al., "Understanding Correlation", https://www.allaboutcircuits.com/technical-articles/understanding-correlation/, Jan. 4, 2017.
Xu, et al.,"A 655 µW Silicon Photomultiplier-Based NIRS/EEG/EIT Monitoring ASIC for Wearable Functional Brain Imaging", IEEE Transactions on Biomedical Circuits and Systems, IEEE, US, vol. 12, No. 6, Dec. 1, 2018.
Zucconi, et al.,"The Autocorrelation Function", https://www.alanzucconi.com/2016/06/06/autocorrelation-function/, Jun. 6, 2016.
Chen, et al., "A PVT Insensitive Field Programmable Gate Array Time-to-digital Converter", 2013 IEEE Nordic-Mediterranean Workshop on Time-To-Digital Converters. Oct. 3, 2013.
Field, et al., "A 100-fps, Time-Correlated Single-PhotonCounting-Based Fluorescence-Lifetime Imager in 130-nm CMOS", IEEE Journal of Solid-State Circuits, vol. 49, No. 4, Apr. 2014.
Lebid, et al., "Multi-Timescale Measurements of Brain Responses in Visual Cortex During Functional Stimulation Using Time-Resolved Spectroscopy", SPIE vol. 5826. Dec. 31, 2005. p. 609, last paragraph—p. 610, paragraph 1.
Zheng, et al., "An Integrated Bias Voltage Control Method for SPAD Arrays", Oct. 1, 2018, IEEE Service Center.
"What are the advantages of multiplexing," Blog, FiberWDM, Mar. 28, 2023. Retrieved on May 9, 2014 from https://www.fiberwdm.com/blog/what-are-the-advantages-of-multiplexing_b101.
Blair, Seraphine. "Multiplexing in modern communication: what it is & advantages," Blog, JAK Electronics, Mar. 12, 2024. Retrieved on May 9, 2024 from https://www.jakelectronics.com/blog/multiplexing.
Nandalal, et al., "Multiplexing," IntechOpen, Sep. 4, 2019. Retrieved on May 9, 2014 from https://www.jakelectronics.com/blog/multiplexing.

* cited by examiner

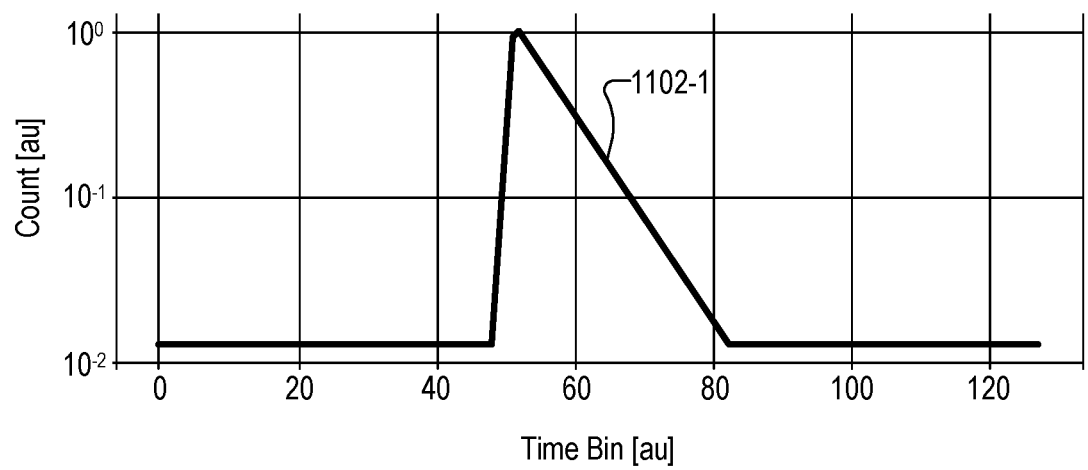
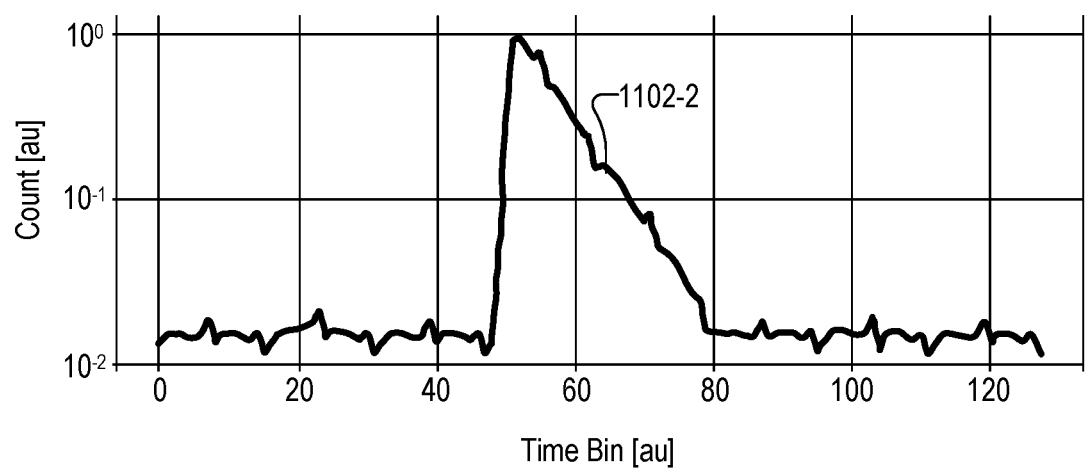
Fig. 11

TECHNIQUES FOR CHARACTERIZING A NONLINEARITY OF A TIME-TO-DIGITAL CONVERTER IN AN OPTICAL MEASUREMENT SYSTEM

RELATED APPLICATIONS

The present application claims priority under 35 U.S.C. § 119(e) to U.S. Provisional Patent Application No. 62/992,502, filed on Mar. 20, 2020, and to U.S. Provisional Patent Application No. 63/059,382, filed on Jul. 31, 2020. These applications are incorporated herein by reference in their respective entireties.

BACKGROUND INFORMATION

Detecting neural activity in the brain (or any other turbid medium) is useful for medical diagnostics, imaging, neuro-engineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

A photodetector capable of detecting a single photon (i.e., a single particle of optical energy) is an example of a non-invasive detector that can be used in an optical measurement system to detect neural activity within the brain. An exemplary photodetector is implemented by a semiconductor-based single-photon avalanche diode (SPAD), which is capable of capturing individual photons with very high time-of-arrival resolution (a few tens of picoseconds).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 11 shows histograms that may be generated by a processing unit.

DETAILED DESCRIPTION

An exemplary optical measurement system (e.g., that implements time of flight detection techniques) may include an array of photodetectors and a corresponding array of time-to-digital converters (TDCs). Each photodetector is configured to detect photons of light after the light is directed to and scattered by a target (e.g., the brain). Each TDC corresponds to a different photodetector and is configured to record timestamp symbols representative of times at which the photons arrive at the photodetectors.

Unfortunately, each TDC in an array of TDCs may have its own nonlinearity characteristics, such as differential nonlinearity (DNL) and integral nonlinearity (INL) characteristics. These nonlinearities may be systematic (e.g., caused by manufacturing process variations, etc.) and/or random, and may skew or otherwise adversely affect measurement operations (e.g., histogram outputs) performed by the optical measurement system. As described herein, these nonlinearities may adversely affect a histogram and/or other measurements generated by the optical measurement system.

Accordingly, the systems, circuits, and methods described herein may be configured to characterize a nonlinearity of a TDC and, in some cases, compensate for the nonlinearity. In this manner, measurement results (e.g., histograms) output by the optical measurement system may not be skewed or otherwise adversely affected by the nonlinearity of a particular TDC. This may make photon detection operation of the optical measurement system more accurate and effective.

These and other advantages and benefits of the present systems, circuits, and methods are described more fully herein.

Figure 1:
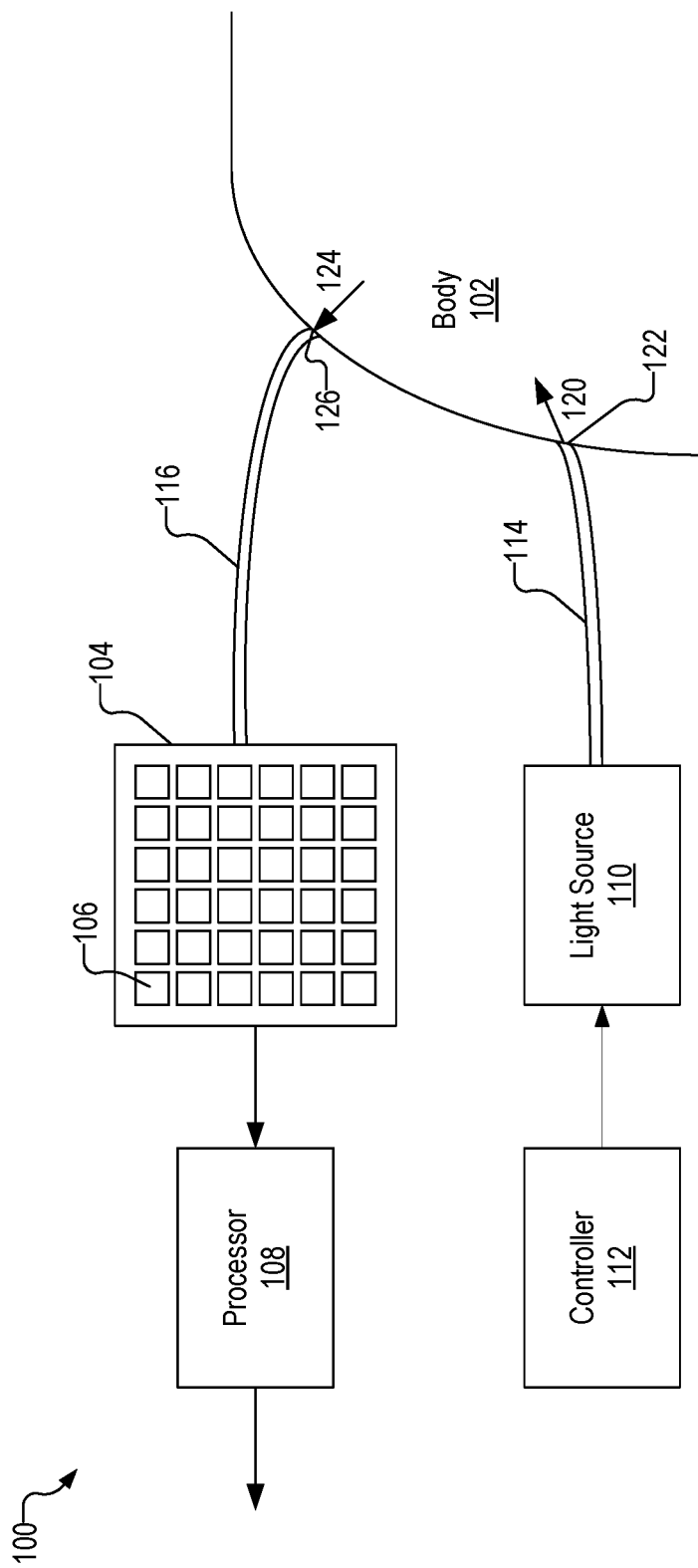
FIG. 1 shows an exemplary optical measurement system.

FIG. 1 shows an exemplary optical measurement system 100 configured to perform an optical measurement operation with respect to a body 102. Optical measurement system 100 may, in some examples, be portable and/or wearable by a user. Optical measurement systems that may be used in connection with the embodiments described herein are described more fully in U.S. patent application Ser. No. 17/176,315, filed Feb. 16, 2021; U.S. patent application Ser. No. 17/176,309, filed Feb. 16, 2021; U.S. patent application Ser. No. 17/176,460, filed Feb. 16, 2021; U.S. patent application Ser. No. 17/176,470, filed Feb. 16, 2021; U.S. patent application Ser. No. 17/176,487, filed Feb. 16, 2021; U.S. patent application Ser. No. 17/176,539, filed Feb. 16, 2021; U.S. patent application Ser. No. 17/176,560, filed Feb. 16, 2021; and U.S. patent application Ser. No. 17/176,466, filed Feb. 16, 2021, which applications are incorporated herein by reference in their entirety.

In some examples, optical measurement operations performed by optical measurement system 100 are associated with a time domain-based optical measurement technique. Example time domain-based optical measurement techniques include, but are not limited to, TCSPC, time domain near infrared spectroscopy (TD-NIRS), time domain diffusive correlation spectroscopy (TD-DCS), and time domain Digital Optical Tomography (TD-DOT).

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light pipes). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as $2^n$ photodetectors (e.g., 256, 512, . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diodes (sLEDs), vertical-cavity surface-emitting lasers (VCSELs), titanium sapphire lasers, micro light emitting diodes (mLEDs), and/or any other suitable laser or light source. In some examples, the light emitted by light source 110 is high coherence light (e.g., light that has a coherence length of at least 5 centimeters) at a predetermined center wavelength.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 may travel via an optical conduit 114 (e.g., a light pipe, a light guide, a waveguide, a single-mode optical fiber, and/or or a multi-mode optical fiber) to body 102 of a subject. In cases where optical conduit 114 is implemented by a light guide, the light guide may be spring loaded and/or have a cantilever mechanism to allow for conformably pressing the light guide firmly against body 102.

Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by arrow 120, the light emitted by light source 110 enters body 102 at a first location 122 on body 102. Accordingly, a distal end of optical conduit 114 may be positioned at (e.g., right above, in physical contact with, or physically attached to) first location 122 (e.g., to a scalp of the subject). In some examples, the light may emerge from optical conduit 114 and spread out to a certain spot size on body 102 to fall under a predetermined safety limit. At least a portion of the light indicated by arrow 120 may be scattered within body 102.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a light guide, a waveguide, a single-mode optical fiber, and/or a multi-mode optical fiber) is positioned at (e.g., right above, in physical contact with, or physically attached to) output location 126 on body 102. In this manner, optical conduit 116 may collect at least a portion of the scattered light (indicated as light 124) as it exits body 102 at location 126 and carry light 124 to detector 104. Light 124 may pass through one or more lenses and/or other optical elements (not shown) that direct light 124 onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., brain tissue, blood flow, etc.) in body 102. Example embodiments of accumulated outputs are described herein.

Figure 2:
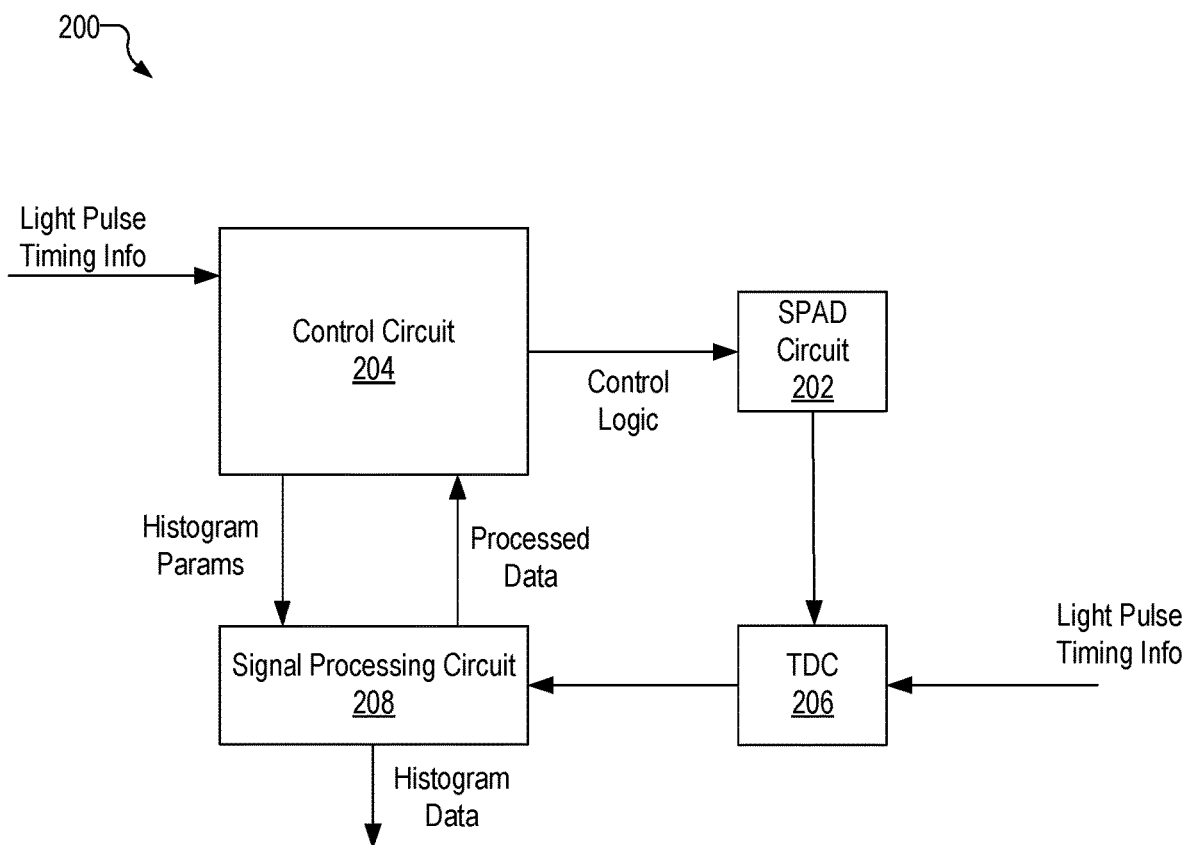
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 includes a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their respective entireties.

In some alternative configurations, SPAD circuit 202 does not include a fast gating circuit. In these configurations, the SPAD included in SPAD circuit 202 may be gated in any suitable manner or be configured to operate in a free running mode with passive quenching.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for a one or more photodetectors 106 and/or TDCs 206.

Figure 3:
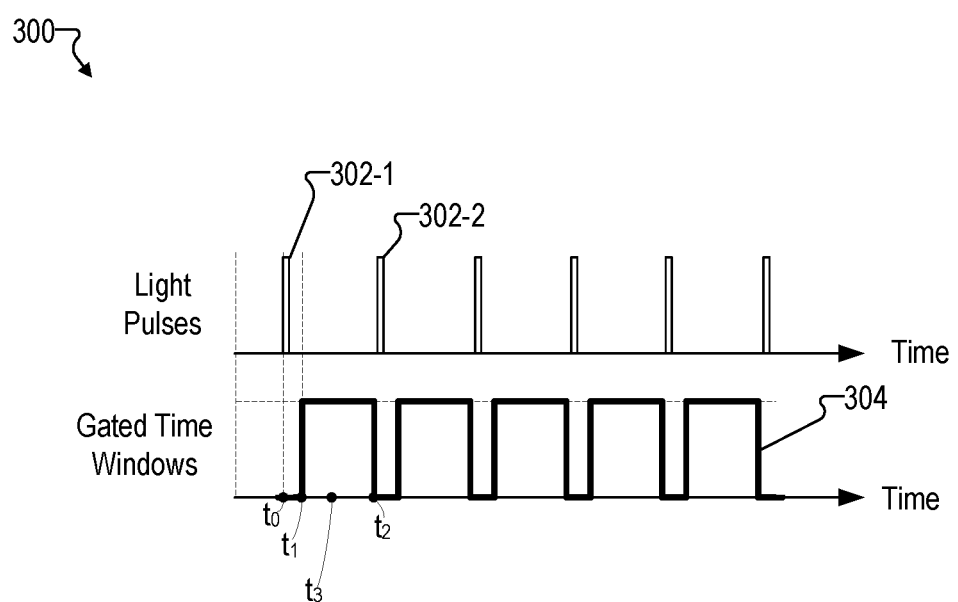
FIG. 3 illustrates an exemplary timing diagram for performing an optical measurement operation using an optical measurement system.

FIG. 3 illustrates an exemplary timing diagram 300 for performing an optical measurement operation using optical measurement system 100. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHZ)). The light pulses may be scattered by the target and then detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

For example, timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. Referring to light pulse 302-1, light pulse 302-1 is applied at a time to. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time to, which may minimize photons detected directly from the laser pulse, before the laser pulse reaches the target. However, in some alternative examples, time $t_1$ is set to be equal to time to.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

As mentioned, in some alternative examples, photodetector 106 may be configured to operate in a free-running mode such that photodetector 106 is not actively armed and disarmed (e.g., at the end of each predetermined gated time window represented by pulse wave 304). In contrast, while operating in the free-running mode, photodetector 106 may be configured to reset within a configurable time period after an occurrence of a photon detection event (i.e., after photodetector 106 detects a photon) and immediately begin detecting new photons. However, only photons detected within a desired time window (e.g., during each gated time window represented by pulse wave 304) may be included in the TPSF.

Figure 4:
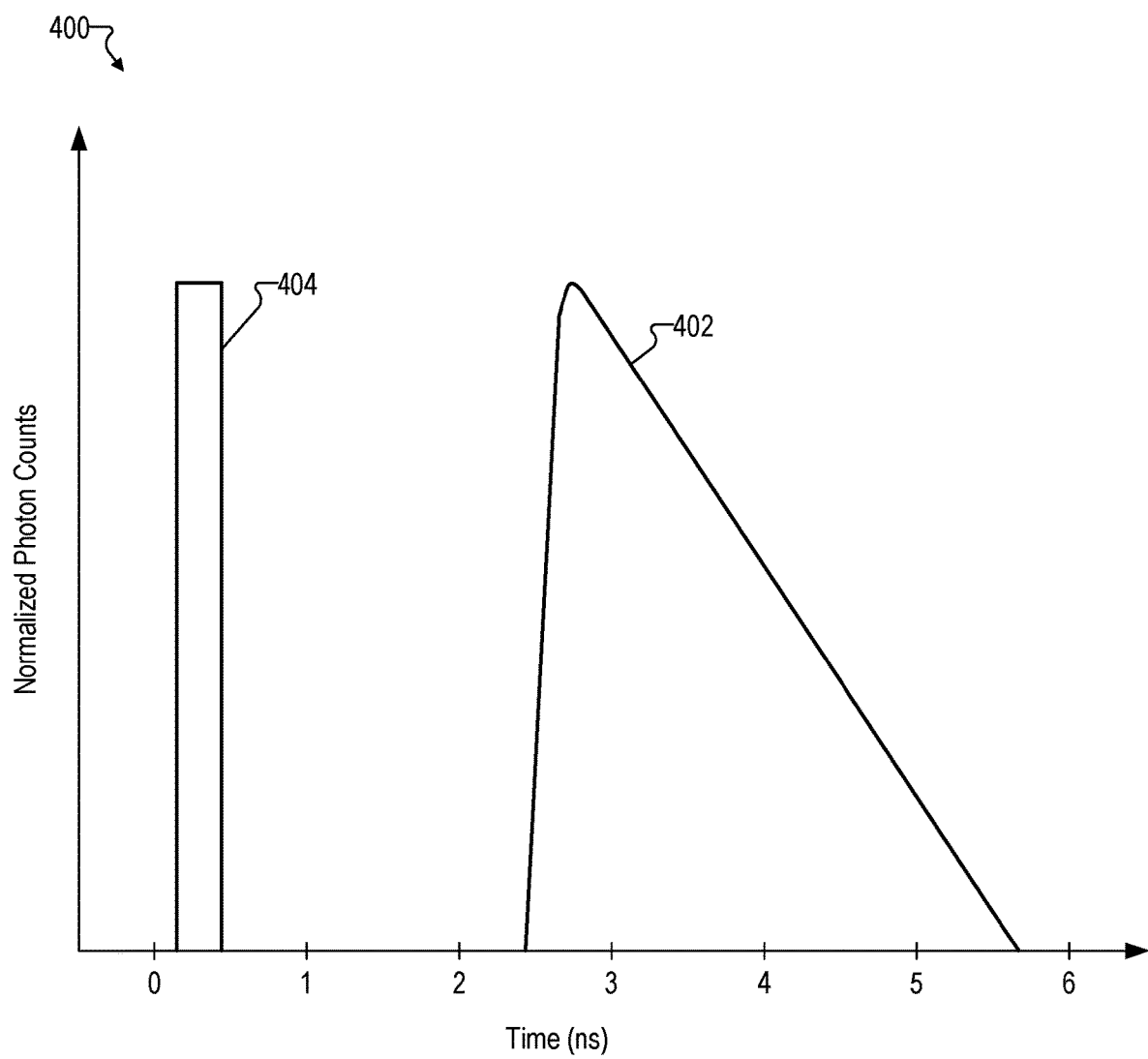
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer detected neural activity.

Optical measurement system 100 may be implemented by or included in any suitable device. For example, optical measurement system 100 may be included, in whole or in part, in a non-invasive wearable device (e.g., a headpiece) that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
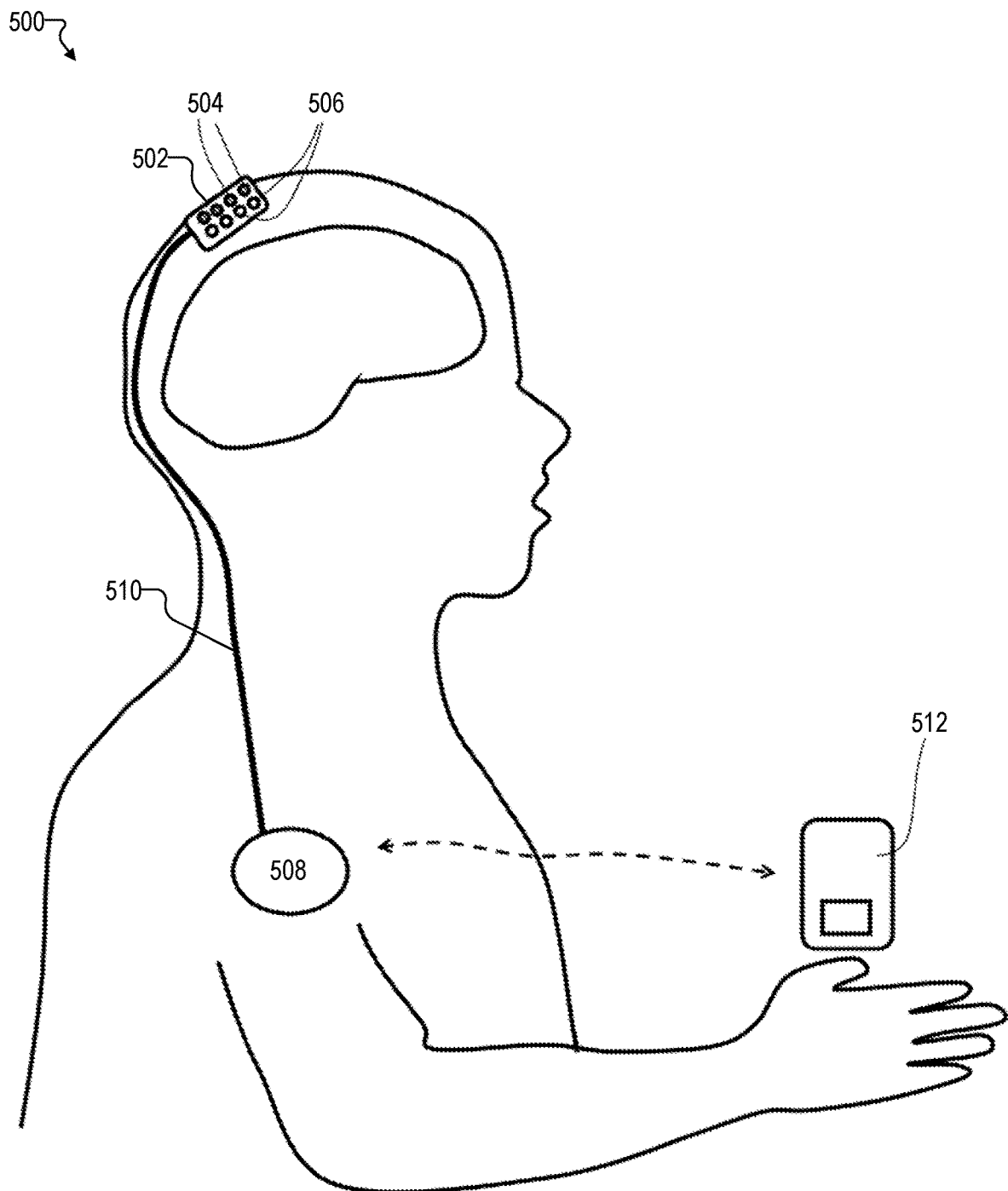
FIG. 5 shows an exemplary non-invasive wearable brain interface system.

FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described more fully in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and for transforming photodetector measurements into an intensity value that represents an optical property of a target within the brain. Brain interface system 500 allows optical detection of deep anatomical locations beyond skin and bone (e.g., skull) by extracting data from photons originating from light source 506 and emitted to a target location within the user's brain, in contrast to conventional imaging systems and methods (e.g., optical coherence tomography (OCT)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detector 504 may be included elsewhere in brain interface system 500. For example, a light source may be included in processor 508 and coupled to head mountable component 502 through optical connections.

Optical measurement system 100 may alternatively be included in a non-wearable device (e.g., a medical device and/or consumer device that is placed near the head or other body part of a user to perform one or more diagnostic, imaging, and/or consumer-related operations). Optical measurement system 100 may alternatively be included in a sub-assembly enclosure of a wearable invasive device (e.g., an implantable medical device for brain recording and imaging).

Optical measurement system 100 may be modular in that one or more components of optical measurement system 100 may be removed, changed out, or otherwise modified as may serve a particular implementation. Additionally or alternatively, optical measurement system 100 may be modular such that one or more components of optical measurement system 100 may be housed in a separate housing (e.g., module) and/or may be movable relative to other components. Exemplary modular multimodal measurement systems are described in more detail in U.S. patent application Ser. No. 17/176,460, filed Feb. 16, 2021, U.S. patent application Ser. No. 17/176,470, filed Feb. 16, 2021, U.S. patent application Ser. No. 17/176,487, filed Feb. 16, 2021, U.S. Provisional Patent Application No. 63/038,481, filed Jun. 12, 2020, and U.S. patent application Ser. No. 17/176,560, filed Feb. 16, 2021, which applications are incorporated herein by reference in their respective entireties.

Figure 6:
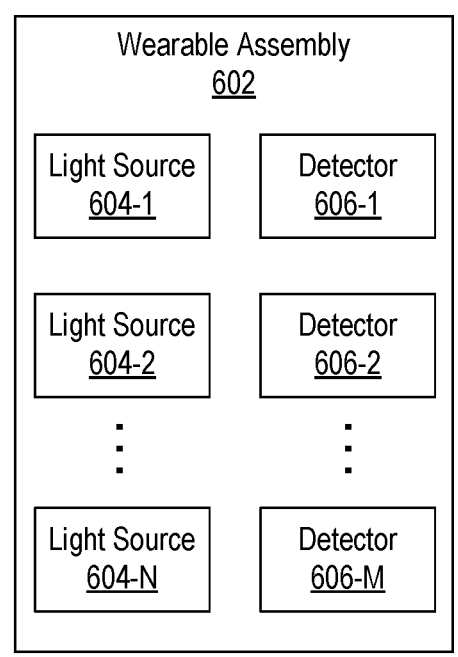
FIG. 6 shows an exemplary optical measurement system.

FIG. 6 shows an exemplary optical measurement system 600 in accordance with the principles described herein. Optical measurement system 600 may be an implementation of optical measurement system 100 and, as shown, includes a wearable assembly 602, which includes N light sources 604 (e.g., light sources 604-1 through 604-N) and M detectors 606 (e.g., detectors 606-1 through 606-M). Optical measurement system 600 may include any of the other components of optical measurement system 100 as may serve a particular implementation. N and M may each be any suitable value (i.e., there may be any number of light sources 604 and detectors 606 included in optical measurement system 600 as may serve a particular implementation).

Light sources 604 are each configured to emit light (e.g., a sequence of light pulses) and may be implemented by any of the light sources described herein. Detectors 606 may each be configured to detect arrival times for photons of the light emitted by one or more light sources 604 after the light is scattered by the target. For example, a detector 606 may include a photodetector configured to generate a photodetector output pulse in response to detecting a photon of the light and a TDC configured to record a timestamp symbol in response to an occurrence of the photodetector output pulse, the timestamp symbol representative of an arrival time for the photon (i.e., when the photon is detected by the photodetector).

Wearable assembly 602 may be implemented by any of the wearable devices, modular assemblies, and/or wearable units described herein. For example, wearable assembly 602 may be implemented by a wearable device (e.g., headgear) configured to be worn on a user's head. Wearable assembly 602 may additionally or alternatively be configured to be worn on any other part of a user's body.

Optical measurement system 600 may be modular in that one or more components of optical measurement system 600 may be removed, changed out, or otherwise modified as may serve a particular implementation. As such, optical measurement system 600 may be configured to conform to three-dimensional surface geometries, such as a user's head. Exemplary modular optical measurement systems comprising a plurality of wearable modules are described in more detail in U.S. Provisional Patent Application No. 62/992,550, filed Mar. 20, 2020, U.S. Provisional Patent Application No. 63/038,459, filed Jun. 12, 2020, and U.S. Provisional Patent Application No. 63/038,468, filed Jun. 12, 2020, which applications are incorporated herein by reference in their respective entireties.

Figure 7:
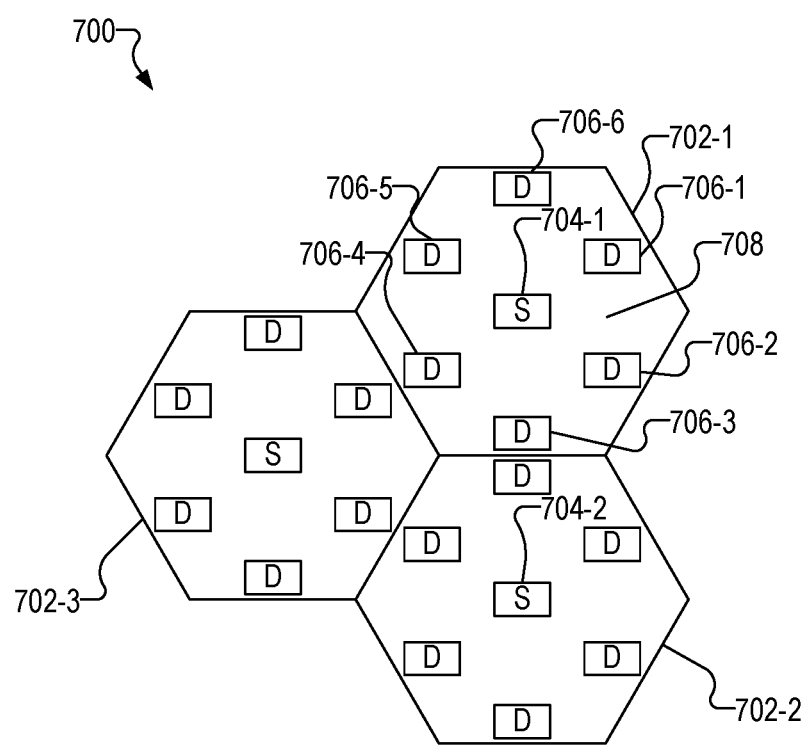
FIG. 7 shows an illustrative modular assembly.

FIG. 7 shows an illustrative modular assembly 700 that may implement optical measurement system 600. Modular assembly 700 is illustrative of the many different implementations of optical measurement system 600 that may be realized in accordance with the principles described herein.

As shown, modular assembly 700 includes a plurality of modules 702 (e.g., modules 702-1 through 702-3). While three modules 702 are shown to be included in modular assembly 700, in alternative configurations, any number of modules 702 (e.g., a single module up to sixteen or more modules) may be included in modular assembly 700.

Each module 702 includes a light source (e.g., light source 704-1 of module 702-1 and light source 704-2 of module 702-2) and a plurality of detectors (e.g., detectors 706-1 through 706-6 of module 702-1). In the particular implementation shown in FIG. 7, each module 702 includes a single light source and six detectors. Each light source is labeled "S" and each detector is labeled "D".

Each light source depicted in FIG. 7 may be implemented by one or more light sources similar to light source 110 and may be configured to emit light directed at a target (e.g., the brain).

Each light source depicted in FIG. 7 may be located at a center region of a surface of the light source's corresponding module. For example, light source 704-1 is located at a center region of a surface 708 of module 702-1. In alternative implementations, a light source of a module may be located away from a center region of the module.

Each detector depicted in FIG. 7 may implement or be similar to detector 104 and may include a plurality of photodetectors (e.g., SPADs) as well as other circuitry (e.g., TDCs), and may be configured to detect arrival times for photons of the light emitted by one or more light sources after the light is scattered by the target.

The detectors of a module may be distributed around the light source of the module. For example, detectors 706 of module 702-1 are distributed around light source 704-1 on surface 708 of module 702-1. In this configuration, detectors 706 may be configured to detect photon arrival times for photons included in light pulses emitted by light source 704-1. In some examples, one or more detectors 706 may be close enough to other light sources to detect photon arrival times for photons included in light pulses emitted by the other light sources. For example, because detector 706-3 is adjacent to module 702-2, detector 706-3 may be configured to detect photon arrival times for photons included in light pulses emitted by light source 704-2 (in addition to detecting photon arrival times for photons included in light pulses emitted by light source 704-1).

In some examples, the detectors of a module may all be equidistant from the light source of the same module. In other words, the spacing between a light source (i.e., a distal end portion of a light source optical conduit) and the detectors (i.e., distal end portions of optical conduits for each detector) are maintained at the same fixed distance on each module to ensure homogeneous coverage over specific areas and to facilitate processing of the detected signals. The fixed spacing also provides consistent spatial (lateral and depth) resolution across the target area of interest, e.g., brain tissue. Moreover, maintaining a known distance between the light source, e.g., light emitter, and the detector allows subsequent processing of the detected signals to infer spatial (e.g., depth localization, inverse modeling) information about the detected signals. Detectors of a module may be alternatively disposed on the module as may serve a particular implementation.

Figure 8A:
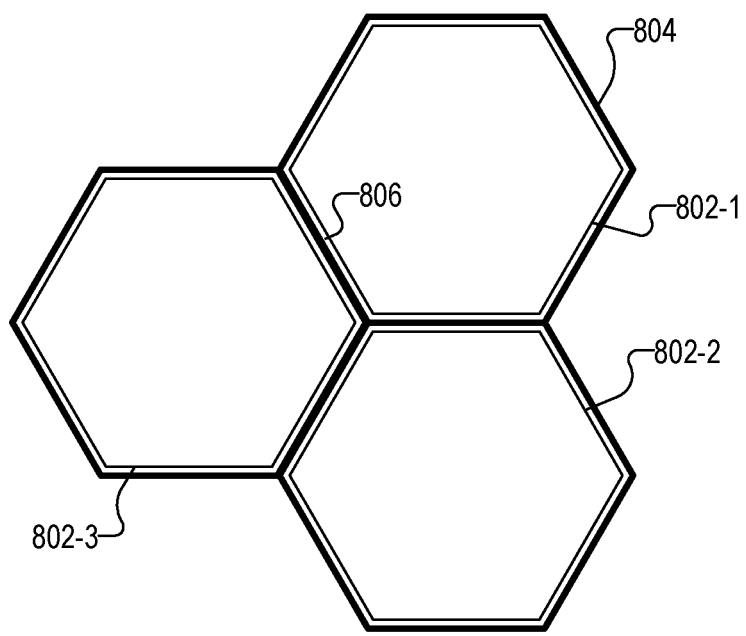
FIGS. 8A-8B show an exemplary implementation of the modular assembly of FIG. 7.
Figure 8B:
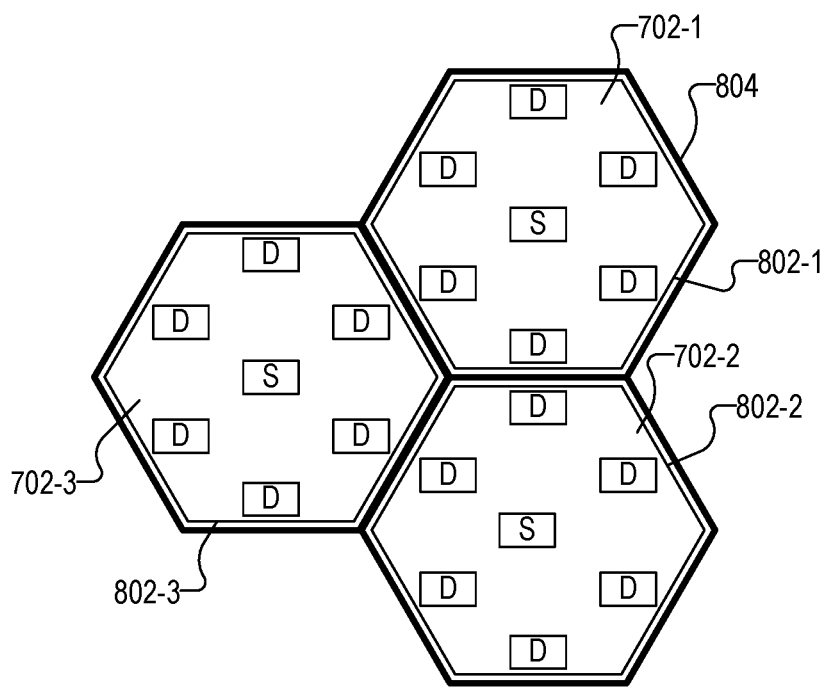

In FIG. 7, modules 702 are shown to be adjacent to and touching one another. Modules 702 may alternatively be spaced apart from one another. For example, FIGS. 8A-8B show an exemplary implementation of modular assembly 700 in which modules 702 are configured to be inserted into individual slots 802 (e.g., slots 802-1 through 802-3, also referred to as cutouts) of a wearable assembly 804. In particular, FIG. 8A shows the individual slots 802 of the wearable assembly 804 before modules 702 have been inserted into respective slots 802, and FIG. 8B shows wearable assembly 804 with individual modules 702 inserted into respective individual slots 802.

Wearable assembly 804 may implement wearable assembly 602 and may be configured as headgear and/or any other type of device configured to be worn by a user.

As shown in FIG. 8A, each slot 802 is surrounded by a wall (e.g., wall 806) such that when modules 702 are inserted into their respective individual slots 802, the walls physically separate modules 702 one from another. In alternative embodiments, a module (e.g., module 702-1) may be in at least partial physical contact with a neighboring module (e.g., module 702-2).

Each of the modules described herein may be inserted into appropriately shaped slots or cutouts of a wearable assembly, as described in connection with FIGS. 8A-8B. However, for ease of explanation, such wearable assemblies are not shown in the figures.

As shown in FIGS. 7 and 8B, modules 702 may have a hexagonal shape. Modules 702 may alternatively have any other suitable geometry (e.g., in the shape of a pentagon, octagon, square, rectangular, circular, triangular, free-form, etc.).

As mentioned, the optical measurement systems described herein may be configured to perform time of flight measurements. By definition, time of flight measures the time taken of an object or wave to travel a distance through a diffuse medium. When used in optical diffuse imaging, a light pulse is applied to a diffuse medium (also referred to herein as a target). After the light pulse is scattered by the diffuse medium, a detector similar to any of the detectors described herein may detect photons of the light pulse. A TDC is used to record timestamp symbols representative of times at which the photon detection events occur.

Figure 9:
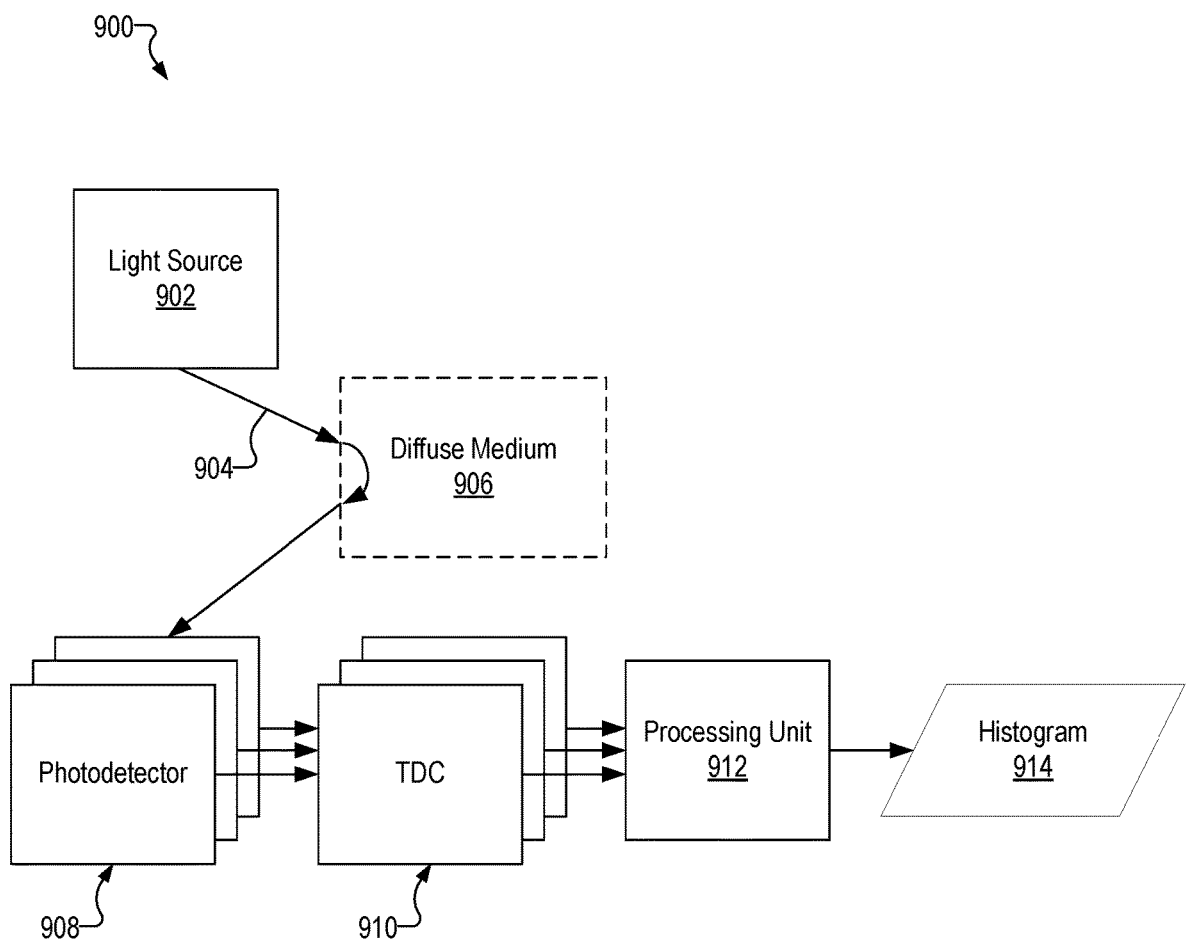
FIG. 9 shows an exemplary implementation of any of the optical measurement systems described herein.

To illustrate, FIG. 9 shows an exemplary implementation 900 of any of the optical measurement systems described herein. As shown, a light source 902 emits a light pulse (represented by line 904), which is directed towards a diffuse medium 906 (e.g., a biological sample, such as the brain and/or any other target within a user). The diffuse medium 906 scatters the light pulse such that some of the photons of the light pulse are directed towards a photodetector array 908. Photodetector array 908 may include any suitable plurality of photodetectors and may be configured to detect photon arrivals with respect to the light pulse emitted by light source 902. A TDC array 910 is configured to convert these photon arrival events into timestamps representing the difference in time between the light pulse and the detection of the photons.

As shown, a processing unit 912 may be configured to receive output signals from TDC array 910. Processing unit 912 may be configured to use the output signals to generate a histogram 914, e.g., by integrating photon detection events from many photodetectors and over many light pulses.

Processing unit 912 may be implemented by processor 108, controller 112, control circuit 204, and/or any other suitable processing and/or computing device or circuit.

Figure 10:
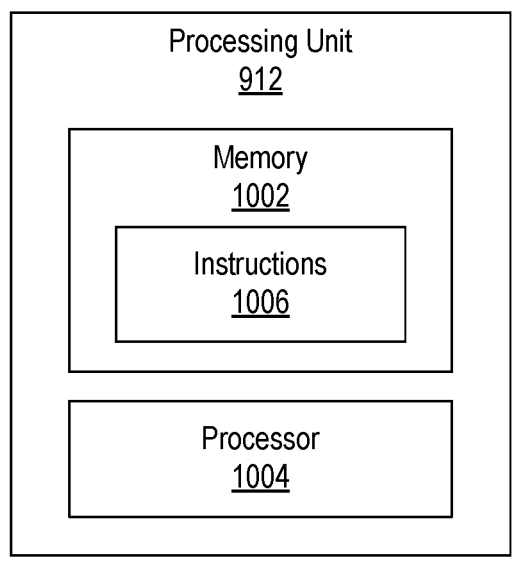
FIG. 10 illustrates an exemplary processing unit.

For example, FIG. 10 illustrates an exemplary implementation of processing unit 912 in which processing unit 912 includes a memory 1002 and a processor 1004 configured to be selectively and communicatively coupled to one another. In some examples, memory 1002 and processor 1004 may be distributed between multiple devices and/or multiple locations as may serve a particular implementation.

Memory 1002 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 1002 may maintain (e.g., store) executable data used by processor 1004 to perform one or more of the operations described herein. For example, memory 1002 may store instructions 1006 that may be executed by processor 1004 to perform any of the operations described herein. Instructions 1006 may be implemented by any suitable application, program (e.g., sound processing program), software, code, and/or other executable data instance. Memory 1002 may also maintain any data received, generated, managed, used, and/or transmitted by processor 1004.

Processor 1004 may be configured to perform (e.g., execute instructions 1006 stored in memory 1002 to perform) various operations described herein. For example, processor 1004 may be configured to perform any of the operations described herein as being performed by processing unit 912.

As mentioned, inherent nonlinearities in each TDC of TDC array 910 may distort the histogram 914 generated by processing unit 912. Such distortions may show up as deviations in histogram 914.

To illustrate, FIG. 11 shows an ideal histogram 1102-1 that may be generated by processing unit 912 based on output signals from TDCs (e.g., TDCs included in TDC array 910) that do not have nonlinearities. FIG. 11 also shows an actual histogram 1102-2 that that may be generated by processing unit 912 based on output signals from TDCs (e.g., TDCs included in TDC array 910) that do have nonlinearities. As shown, histogram 1102-2 includes deviations with respect to histogram 1102-1 for all time bins. These deviations are caused by the nonlinearities of the TDCs.

Figure 12:
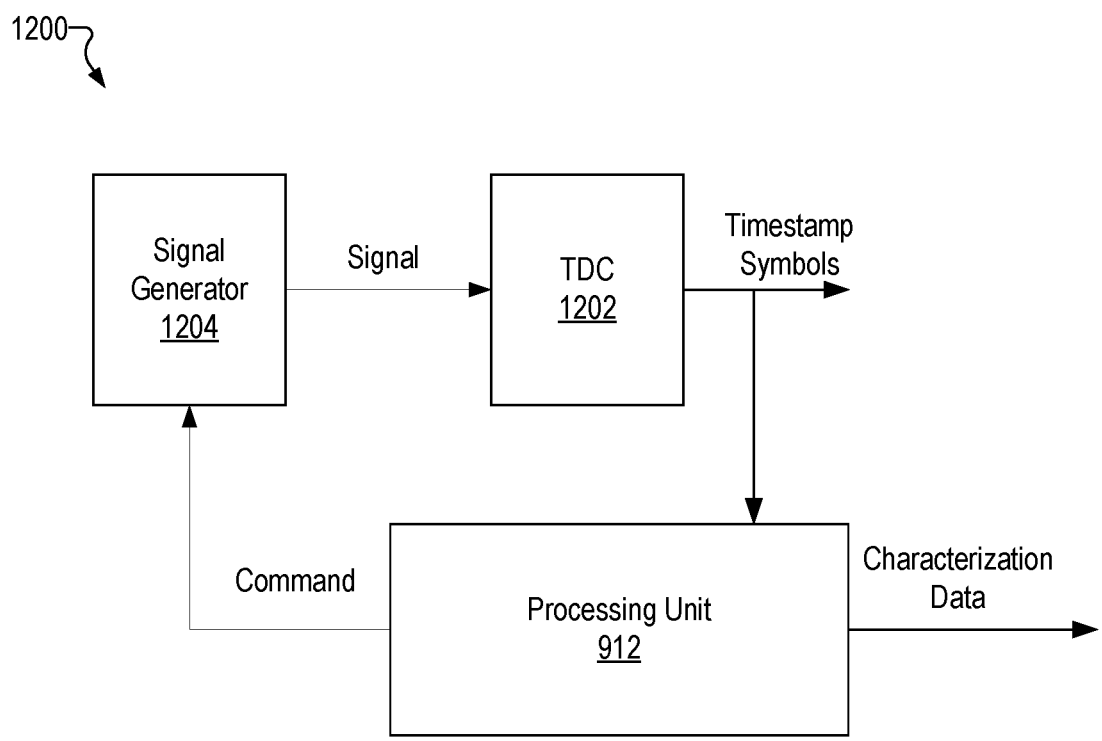
FIG. 12 shows an exemplary configuration that may be used to characterize a nonlinearity of a time-to-digital converter.

The systems, circuits, and methods described herein are accordingly configured to characterize and, in some cases, compensate for the nonlinearities of one or more TDCs. FIG. 12 shows an exemplary configuration 1200 that may be used to characterize a nonlinearity of a TDC 1202 (e.g., any of the TDCs described herein) included in an optical measurement system (e.g., any of the optical measurement systems described herein. As shown, configuration 1200 may include a signal generator 1204 and processing unit 912 in communication with one another. In some examples, signal generator 1204 and/or processing unit 912 are include in a wearable assembly (e.g., wearable assembly 602 of FIG. 6) configured to be worn by a user.

As shown, processing unit 912 may be configured to transmit a command to signal generator 1204 that directs signal generator 1204 to apply a signal to TDC 1202. TDC 1202 may be configured to record timestamp symbols in response to the applied signal. Processing unit 912 may generate, based on the timestamp symbols recorded by TDC 1202 in response to the signal, characterization data representative of a nonlinearity of TDC 1202. Based on the characterization data, processing unit 912 may, in some cases, perform an action associated with TDC 1202. Examples of this are described herein.

Signal generator 1204 may be implemented by any suitable circuitry configured to generate a signal (e.g., an electrical signal or an optical signal) that may be applied to TDC 1202. Illustrative implementations of signal generator 1204 will now be described.

In some examples, signal generator 1204 may be implemented by a precision timing circuit configured to generate output pulses having either programmable delays or programmable pulse widths. In these examples, the signal output by signal generator 1204 may include a sequence of these output pulses and processing unit 912 may be configured to direct signal generator 1204 to apply the signal to TDC 1202 by directing the precision timing circuit to sweep the output pulses across either a plurality of delays or a plurality of pulse widths. TDC 1202 may be configured to record timestamp symbols as the output pulses are swept across the plurality of delays or the plurality of pulse widths.

Figure 13:
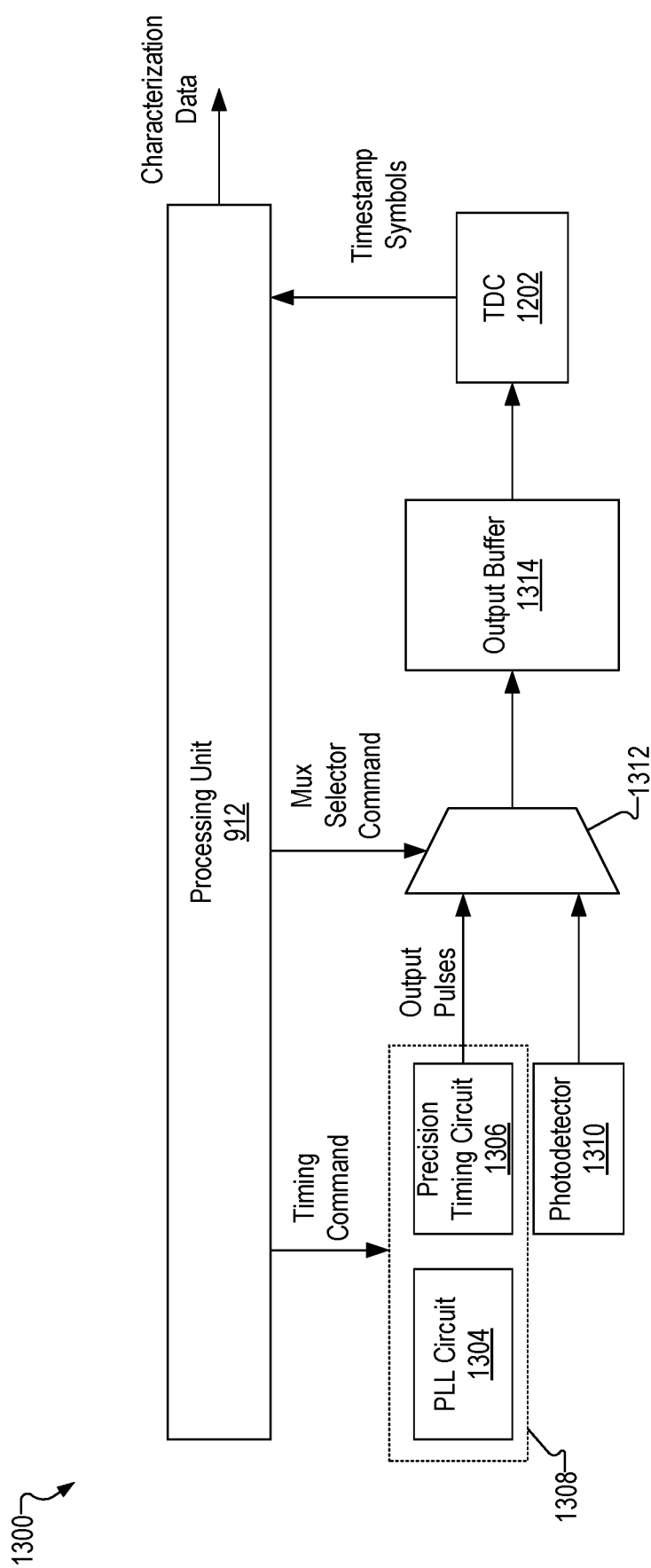
FIG. 13 shows an exemplary implementation of the configuration shown in FIG. 12.

To illustrate, FIG. 13 shows an exemplary implementation 1300 of configuration 1200 in which signal generator 1204 is implemented by a phase locked loop (PLL) circuit 1304 and a precision timing circuit 1306. PLL circuit 1304 and precision timing circuit 1306 together constitute a PLL circuit based architecture 1308. Implementation 1300 further includes a photodetector 1310 corresponding to TDC 1202, a multiplexer 1312, and an output buffer 1314.

Multiplexer 1312 is configured to selectively pass, to TDC 1202 (e.g., by way of output buffer 1314), output pulses generated by precision timing circuit 1306 or a photodetector output pulse output by photodetector 1310. Processing unit 912 may control multiplexer 1312 by providing a MUX selector command to multiplexer 1312. For example, the MUX selector command may cause multiplexer 1312 to selectively pass the output pulses generated by precision timing circuit 1306 to TDC 1202 when it is desired to characterize a nonlinearity of TDC 1202 (e.g., during a calibration mode). By causing multiplexer 1312 to pass the output pulses to TDC 1202 instead of passing photodetector output pulses output by photodetector 1310, processing unit 912 may electrically bypass photodetector 1310. As such, implementation 1300 may be referred to as an electrical bypass implementation.

As shown, output buffer 1314 is in series with an output of multiplexer 1312. In this configuration, the output of multiplexer 1312 is passed to TDC 1202 by way of output buffer 1314. In some alternative configurations, output buffer 1314 is omitted such that the output of multiplexer 1312 is passed directly to TDC 1202.

PLL circuit 1304 is configured to have a PLL feedback period. The output pulses generated by precision timing circuit 1306 may have programmable delays (also referred to as programmable temporal positions) and/or programmable pulse widths within the PLL feedback period. These programmable delays or pulse widths may be specified by a timing command provided by processing unit 912. In this manner, as described herein, the output pulses may be used to characterize a nonlinearity TDC 1202.

Figure 14:
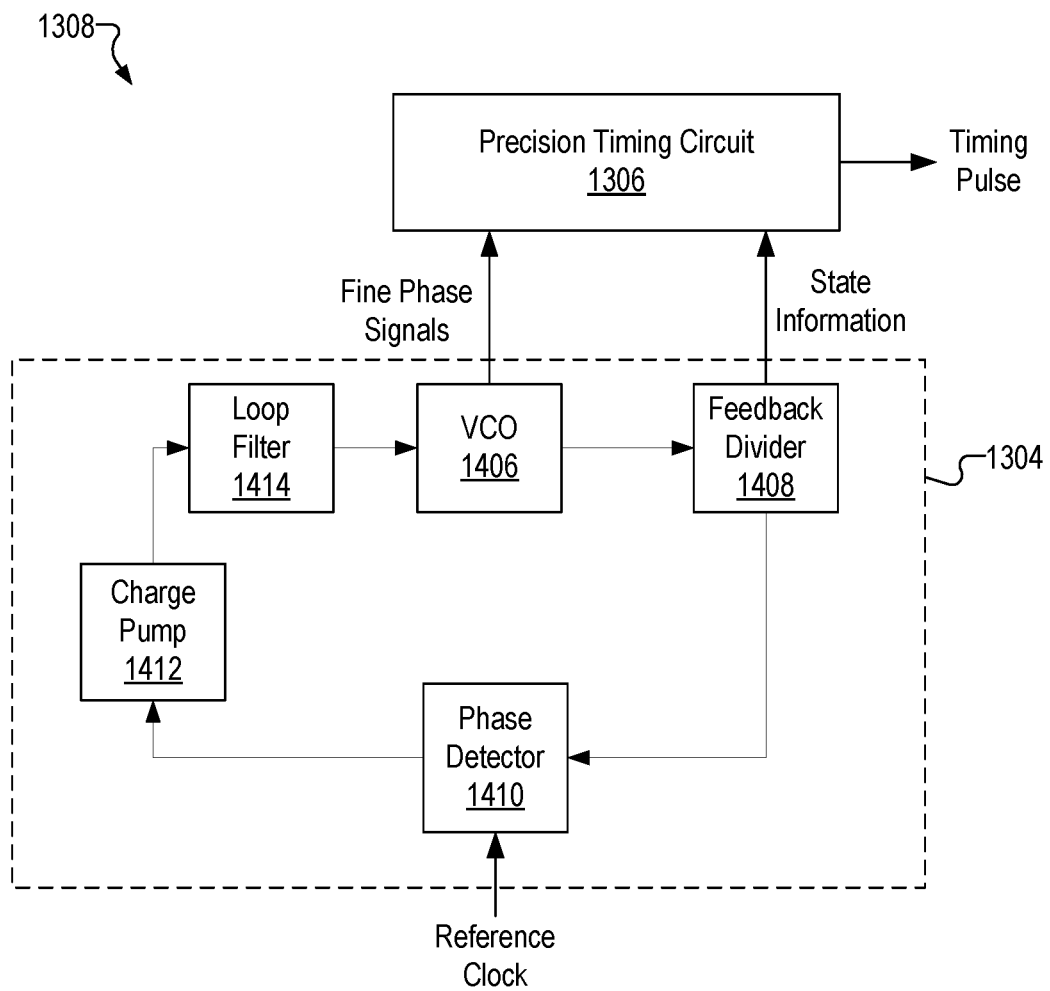
FIG. 14 illustrates an exemplary implementation of a phase locked loop circuit based architecture.

FIG. 14 illustrates an exemplary implementation of PLL circuit based architecture 1308. PLL circuit based architecture 1308 may be configured to generate and set a temporal position (e.g., of a rising edge and/or of a falling edge) of a timing pulse that may be used to set a delay and/or pulse width of one or more output pulses described herein.

As shown, architecture 1308 includes PLL circuit 1304 communicatively coupled to precision timing circuit 1306. PLL circuit 1304 includes a VCO 1406, a feedback divider 1408, a phase detector 1410, a charge pump 1412, and a loop filter 1414 connected in a feedback loop configuration. Phase detector 1410 may receive a reference clock as an input such that PLL circuit 1304 has a PLL feedback period defined by the reference clock. The reference clock may have any suitable frequency, such as any frequency between 1 MHz and 200 MHz.

VCO 1406 may be implemented by any suitable combination of circuitry (e.g., a differential multi-stage gated ring oscillator (GRO) circuit) and is configured to lock to the reference clock (i.e., to a multiple of a frequency of the reference clock). To that end, VCO 1406 may include a plurality of stages configured to output a plurality of fine phase signals each having a different phase and uniformly distributed in time. In some examples, each stage may output two fine phase signals that have complimentary phases. VCO 1406 may include any suitable number of stages configured to output any suitable number of fine phase signals (e.g., eight stages that output sixteen fine phase signals). The duration of a fine phase signal pulse depends on the oscillator frequency of VCO 1406 and the total number of fine phase signals. For example, if the oscillator frequency is 1 gigahertz (GHz) and the total number of fine phase signals is sixteen, the duration of a pulse included in a fine phase signal is 1 GHz/16, which is 62.5 picoseconds (ps). As described herein, these fine phase signals may provide precision timing circuit 1306 with the ability to adjust a phase (i.e., temporal position) of a timing pulse with relatively fine resolution.

Feedback divider 1408 is configured to be clocked by a single fine phase signal included in the plurality of fine phase signals output by VCO 1406 and have a plurality of feedback divider states during the PLL feedback period. The number of feedback divider states depends on the oscillator frequency of VCO 1406 and the frequency of the reference clock. For example, if the oscillator frequency is 1 gigahertz (GHz) and the reference clock has a frequency of 50 MHz, the number of feedback divider states is equal to 1 GHz/50 MHZ, which is equal to 20 feedback divider states. As described herein, these feedback divider states may provide precision timing circuit 1306 with the ability to adjust a phase (i.e., temporal position) of a timing pulse with relatively course resolution.

Feedback divider 1408 may be implemented by any suitable circuitry. In some alternative examples, feedback divider 1408 is at least partially integrated into precision timing circuit 1306.

As shown, the fine phase signals output by VCO 1406 and state information (e.g., signals and/or data) representative of the feedback divider states within feedback divider 1408 are input into precision timing circuit 1306. Precision timing circuit 1306 may be configured to generate a timing pulse and set, based on a combination of one of the fine phase signals and one of the feedback dividers states, a temporal position of the timing pulse within the PLL feedback period. For example, if there are N total fine phase signals and M total feedback divider states, precision timing circuit 1306 may set the temporal position of the timing pulse to be one of N times M possible temporal positions within the PLL feedback period. To illustrate, if N is 16 and M is 20, and if the duration of a pulse included in a fine phase signal is 62.5 ps, the temporal position of the timing pulse may be set to be one of 320 possible positions in 62.5 ps steps.

The timing pulse generated by precision timing circuit 1306 may be used within any of the optical measurement systems described herein in any suitable manner. For example, the timing pulse may be configured to trigger a start (e.g., a rising edge) of an output pulse used by a component within an optical measurement system. Alternatively, the timing pulse may be configured to trigger an end (e.g., a falling edge) of an output pulse used by a component within an optical measurement system. Alternatively, the timing pulse itself may be provided for use as an output pulse used by a component within an optical measurement system. In some examples, precision timing circuit 1306 may generate multiple timing pulses each used for a different purpose within an optical measurement system. PLL circuit based architecture 1308 is described in more detail in U.S. Provisional Patent Application No. 63/027,011, filed May 19, 2020, and incorporated herein by reference in its entirety.

In some examples, processing unit 912 may use the output pulses generated by precision timing circuit 1306 to characterize one or more nonlinearities of TDC 1202. This may be performed in any suitable manner.

For example, processing unit 912 may direct precision timing circuit 1306 to apply the output pulses to TDC 1202 by directing multiplexer 1312 to pass the output pulses to TDC 1202 by way of output buffer 1314 and by directing precision timing circuit 1306 to sweep the output pulses across either a plurality of delays or a plurality of pulse widths within the PLL feedback period. Processing unit 912 may generate, based on timestamp symbols recorded by TDC 1202 as the output pulses are being swept across the delays or pulse widths, characterization data representative of a nonlinearity of TDC 1202. Exemplary manners in which processing unit 912 may generate the characterization data are described herein.

While FIGS. 13-14 show an example in which signal generator 1204 is implemented by a precision timing circuit 1306 configured to generate output pulses, signal generator 1204 may alternatively be implemented by any other suitable component configured to generate output pulses that have programmable delays and/or pulse widths. For example, signal generator 1204 may be implemented by a delay locked loop (DLL)-based circuit, an on-chip precision delay generator, and/or a pulse generator external to an optical measurement system of which TDC 1202 is a part.

Figure 15:
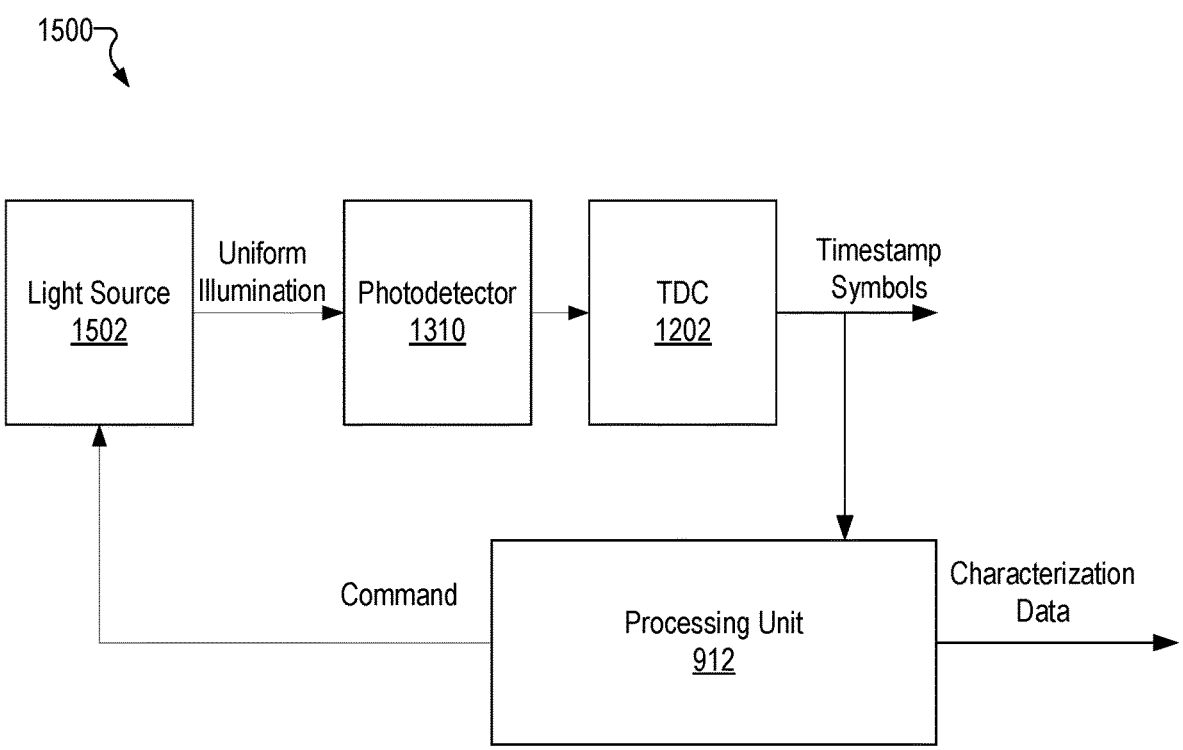
FIG. 15 shows another exemplary implementation of the configuration of FIG. 12.

FIG. 15 shows another exemplary implementation 1500 of configuration 1200 in which signal generator 1204 is implemented by a light source 1502. In implementation 1500, light source 1502 may be implemented by any suitable light source configured to emit temporally uniform illumination (e.g., overhead light or any other type of light that is relatively uniform or constant over time). Light source 1502 may be included in or external to an optical measurement system of which TDC 1202 is a part.

In some examples, processing unit 912 may be configured to provide a command to light source 1502 to begin emitting the uniform illumination. Alternatively, processing unit 912 may not be in communication with light source 1502. In these alternative examples, light source 1502 may be controlled by an external controller and/or manually controlled.

As shown, implementation 1500 further includes the photodetector 1310 that corresponds to TDC 1202. In this configuration, photodetector 1310 is configured to detect photons from the uniform illumination. TDC 1202 is configured to record timestamp symbols corresponding to arrival times for the photons at photodetector 1310. Over time, this may create a uniform probability distribution for triggering photodetector 1310 through the range of TDC 1202 with respect to a reference clock. Based on an output signal of TDC 1202, processing unit 912 may generate characterization data representative of a nonlinearity of TDC 1202. It will be recognized that in this uniform illumination approach, the characterization data is further representative of nonlinearities of photodetector 1310 and the communication path between photodetector 1310 and TDC 1202.

Figure 16:
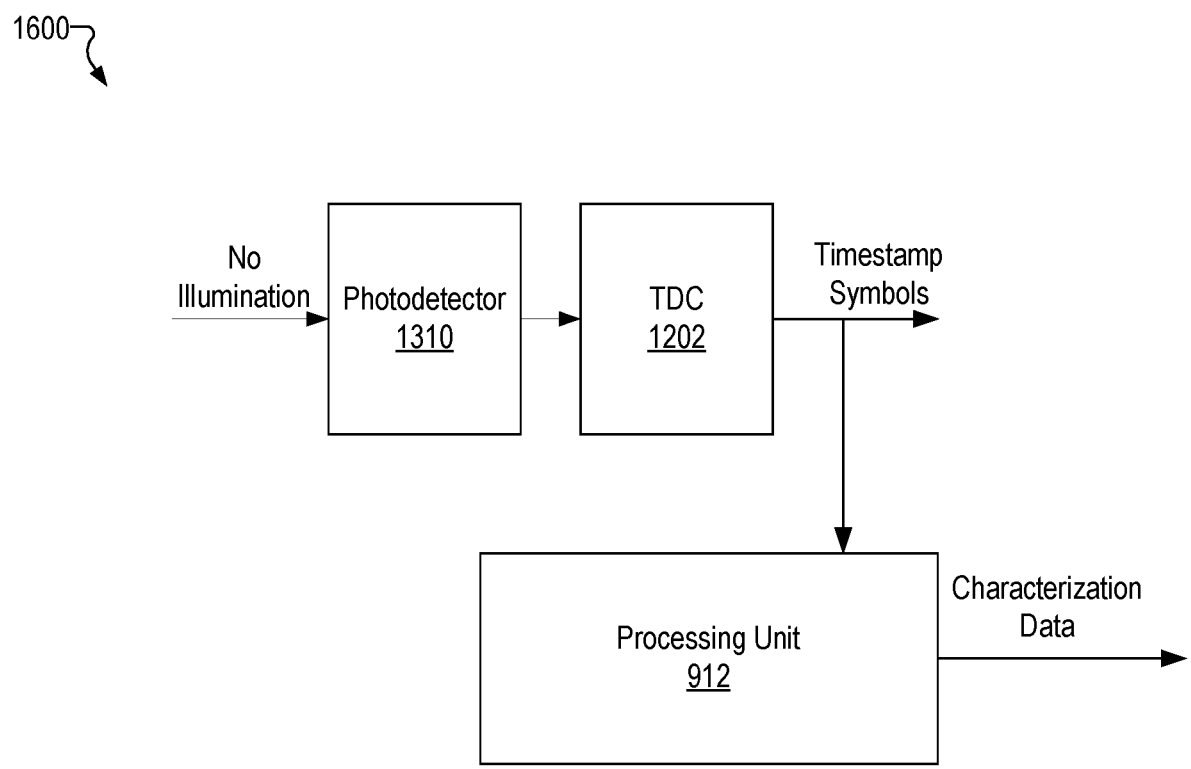
FIG. 16 shows a configuration in which a processing unit is configured to characterize a nonlinearity of a time-to-digital converter.

FIG. 16 shows an alternative configuration 1600 in which processing unit 912 is configured to characterize a nonlinearity of TDC 1202 based on dark counts (e.g., when photodetector 1310 fires even though there is no illumination being applied to photodetector 1310). As shown, configuration 1600 is similar to implementation 1500, except that configuration 1600 does not include a light source. Alternatively, configuration 1600 may include a light source, but processing unit 912 may be configured to prevent the light source from outputting light while the characterization data is generated.

In configuration 1600, photodetector 1310 may fire without any light source due to thermal noise, etc. These dark counts may, over time, create a uniform probability distribution similar to that created in implementation 1500. Based on an output signal of TDC 1202, processing unit 912 may generate characterization data representative of a nonlinearity of TDC 1202. It will be recognized that in this dark count approach, the characterization data is further representative of nonlinearities of photodetector 1310 and the communication path between photodetector 1310 and TDC 1202.

Regardless of how TDC 1202 generates timestamp symbols (e.g., using the electrical bypass configuration of FIG. 13, the uniform illumination configuration of FIG. 15, or the dark count configuration of FIG. 16), processing unit 912 may generate characterization data representative of a nonlinearity of TDC 1202 in any suitable manner. For example, processing unit 912 may generate the characterization data by generating a histogram of the timestamp symbols recorded by TDC 1202 and determining a code density metric for each time bin of the histogram. The code density metric is representative of a density of timestamp symbols at each time bin of the histogram, as "code" is another term for timestamp symbol.

Processing unit 912 may generate a histogram of the timestamp symbols recorded by TDC 1202 in any suitable manner. For example, processing unit 912 may record a total number of counts (e.g., recorded timestamp symbols) that occur during each of a plurality of time bins. The time bins may have any suitable temporal resolution.

Processing unit 912 may be configured to generate the code density metric for each time bin of the histogram in any suitable manner. For example, processing unit 912 may be configured to generate the code density metric for each time bin of the histogram in accordance with following equation:

$$\text{Code density}[i] = \frac{\text{hist\_bin}[i]}{\sum_{all\ bins} \text{hist\_bin}[i]} * B_{total}. \quad \text{(Equation 1)}$$

In Equation 1, Code density[i] is the code density metric, i is an index for each time bin of the histogram, hist_bin[i] represents a value in the histogram at each time bin i, $B_{total}$ represents a total number of time bins in the histogram, and $\sum_{all\ bins}$hist_bin [i] represents a sum of all the values in the histogram.

In some examples, the characterization data generated by processing unit 912 may further include a nonlinearity metric (e.g., a metric representative of DNL and/or INL) for TDC 1202. For example, processing unit 912 may determine, based on the code density metric represented in Equation 1, a nonlinearity metric for each time bin of the histogram generated by processing unit 912. In some examples, this may be performed by normalizing the code density metric of Equation 1 in any suitable manner. For example, processing unit 912 may normalize the code density metric of Equation 1 in accordance with the following equation:

$$\text{DNL}[i] = \text{Code density}[i] - 1 \quad \text{(Equation 2)}.$$

In Equation 2, DNL[i] represents a nonlinearity metric for each time bin i. As shown, the normalization is performed by subtracting a value of 1 from the code density metric for each time bin i.

Processing unit 912 may use the code density metric of Equation 1 and/or the nonlinearity metric of Equation 2 to compensate for a nonlinearity of TDC 1202. This may be performed in any suitable manner. For example, processing unit 912 may compensate for a nonlinearity of TDC 1202 by using the code density metric of Equation 1 to normalize (e.g., linearize and/or calibrate) a transfer function of TDC 1202. This, in turn, can remove at least some of the variations in a histogram generated by processing unit 912 that are caused by the nonlinearity.

To illustrate, processing unit 912 may normalize a transfer function of TDC 1202 in accordance with the following equation:

$$\text{hist\_bin\_norm}[i] = \frac{\text{hist\_bin}[i]}{\text{code density}[i]}. \quad \text{(Equation 3)}$$

In Equation 3, hist_bin_norm[i] represents the normalized transfer function, hist_bin [i] represents a value in the histogram at each time bin i, and code density[i] is the code density metric of Equation 1.

By normalizing the transfer function of TDC 1202, variations in the histogram generated by processing unit 912 based on the output of TDC 1202 may be minimized or eliminated. For example, instead of generating a histogram that looks like histogram 1102-2 (FIG. 11), processing unit 912 may generate a histogram that looks like histogram 1102-1 (FIG. 11) when the transfer function of TDC 1202 is normalized in accordance with Equation 3 or in any other suitable manner.

Processing unit 912 may perform any other suitable action based on the characterization data for TDC 1202. For example, processing unit 912 may rate TDC 1202 based on the characterization data. This rating may be compared to other TDCs (e.g., in the same TDC array). In some examples, if the rating of TDC 1202 is outside a predetermined range of values (e.g., if the rating value deviates too much from a range of rating values for other TDCs in the same TDC array), thereby indicating that TDC 1202 has a relatively poor impulse response function, TDC 1202 and its corresponding photodetector may be disabled so as to not skew an overall histogram generated by optical measurement system 100. TDC 1202 and its corresponding photodetector may be disabled in any suitable manner. For example, processing unit 912 may disable a power supply for TDC 1202 and/or its corresponding photodetector, transmit a control signal to TDC 1202 and/or its corresponding photodetector that turns off or disables TDC 1202 and/or its corresponding photodetector, and/or abstain from transmitting a gate on pulse to the photodetector.

In configurations in which outputs of many TDCs (e.g., each TDC included in an array of TDCs, such as TDC array 910) are combined into a single histogram, processing unit 912 may be configured to isolate each TDC/photodetector pair so that only one TDC/photodetector pair is active at any given time. This may allow a nonlinearity of each individual TDC and/or DCT/photodetector pair to be characterized. For example, while processing unit 912 characterizes a nonlinearity of TDC 1202, processing unit 912 may disable other TDCs within an array of TDCs (e.g., TDC array 910) of which TDC 1202. This may be performed in any suitable manner.

Processing unit 912 may generate characterization data for TDC 1202 at any suitable time. For example, processing unit 912 may generate characterization data for TDC 1202 in response to an event occurring within an optical measurement system of which TDC 1202 is a part. For example, processing unit 912 may generate characterization data for TDC 1202 at startup (e.g., a powering on) of the optical measurement system. As another example, processing unit 912 may be configured to place the optical measurement system in a calibration mode (e.g., during a startup procedure for the optical measurement system) and generate the characterization data while the optical measurement system is in the calibration mode.

As mentioned, optical measurement system 100 may be at least partially wearable by a user. For example, optical measurement system 100 may be implemented by a wearable device configured to be worn by a user (e.g., a head-mountable component configured to be worn on a head of the user). The wearable device may include one or more photodetectors, modules, and/or any of the other components described herein. In some examples, one or more components (e.g., processing unit 912, processor 108, controller 112, etc.) may not be included in the wearable device and/or included in a separate wearable device than the wearable device in which the one or more photodetectors are included. In these examples, one or more communication interfaces (e.g., cables, wireless interfaces, etc.) may be used to facilitate communication between the various components.

FIGS. 17-22 illustrate embodiments of a wearable device 1700 that includes elements of the optical detection systems described herein. In particular, the wearable devices 1700 shown in FIGS. 17-22 include a plurality of modules 1702, similar to the modules described herein. For example, each module 1702 may include a light source (e.g., light source 704-1) and a plurality of detectors (e.g., detectors 706-1 through 706-6). The wearable devices 1700 may each also include a controller (e.g., controller 112) and a processor (e.g., processor 108 or processing unit 912) and/or be communicatively connected to a controller and processor. In general, wearable device 1700 may be implemented by any suitable headgear and/or clothing article configured to be worn by a user. The headgear and/or clothing article may include batteries, cables, and/or other peripherals for the components of the optical measurement systems described herein.

Figure 17:
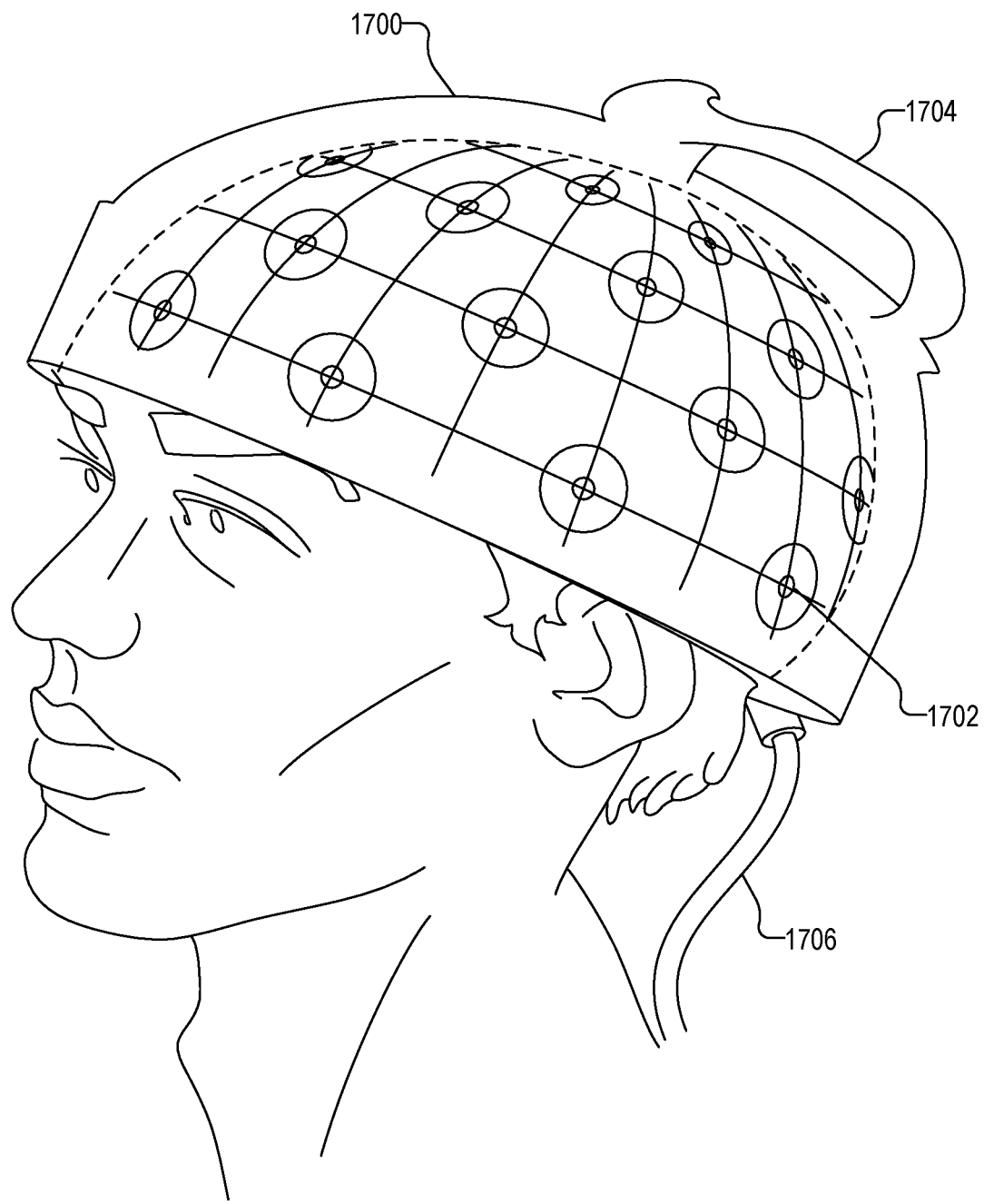
FIGS. 17-22 illustrate embodiments of a wearable device that includes elements of the optical detection systems described herein.
Figure 18:
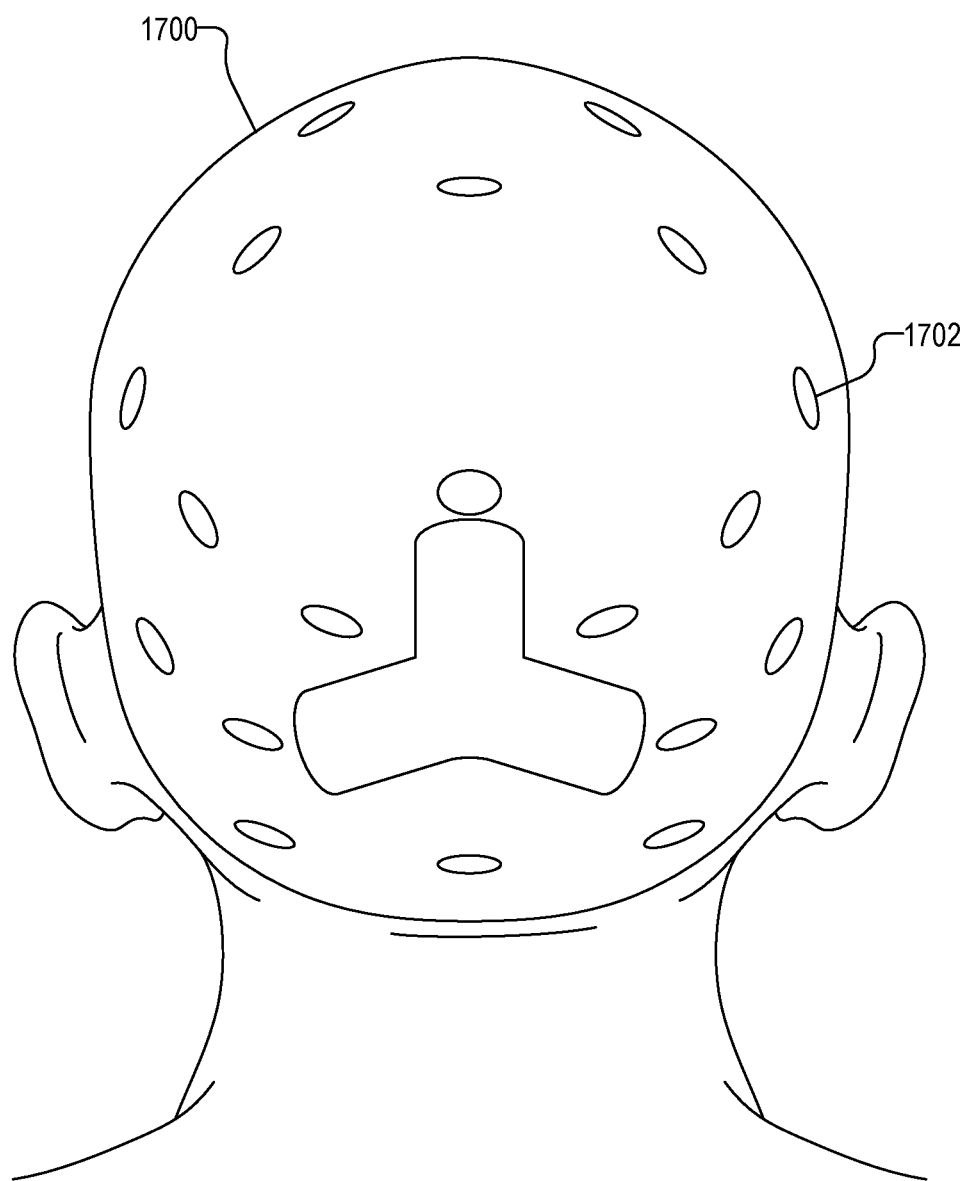
Figure 19:
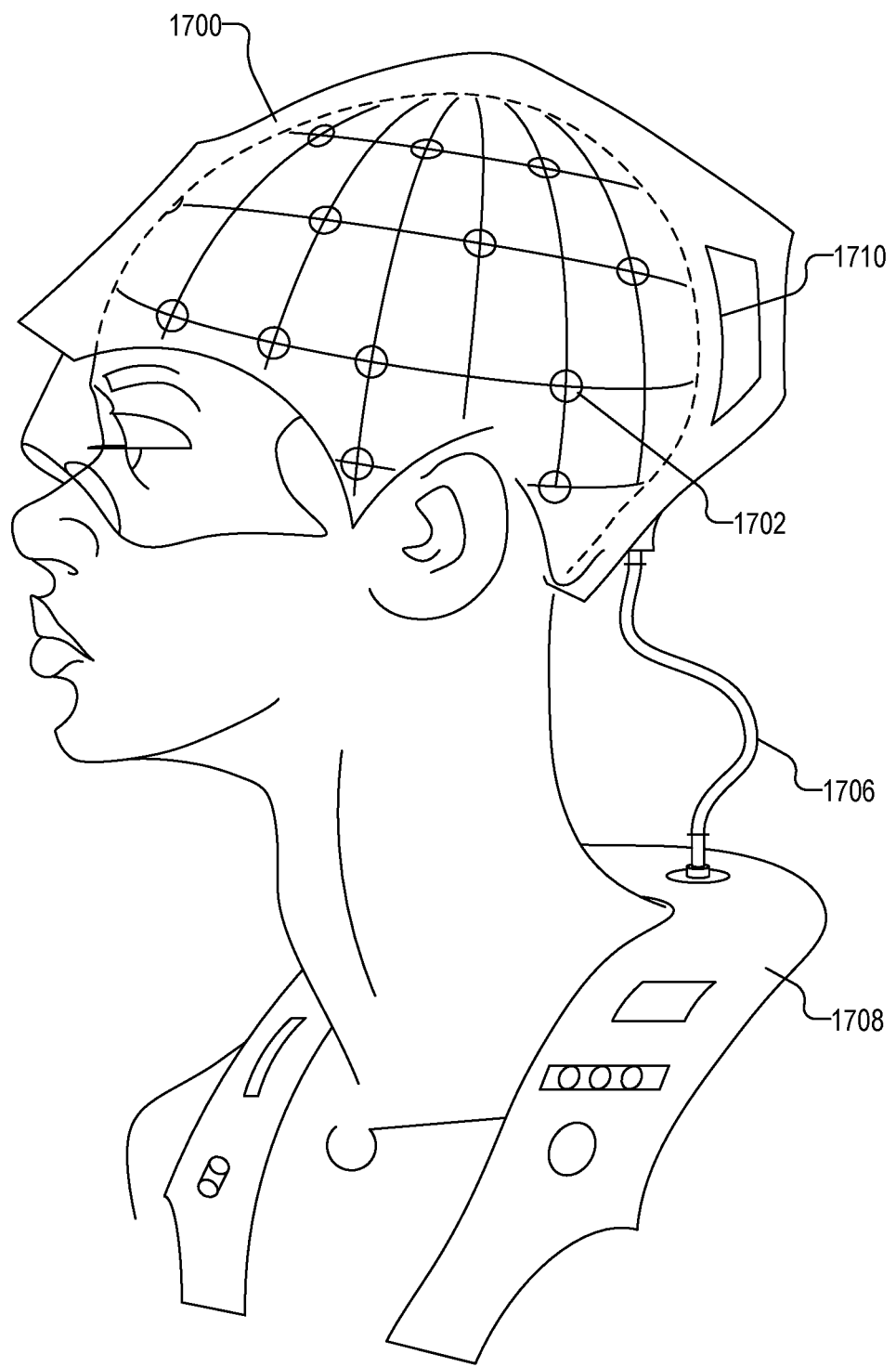

FIG. 17 illustrates an embodiment of a wearable device 1700 in the form of a helmet with a handle 1704. A cable 1706 extends from the wearable device 1700 for attachment to a battery or hub (with components such as a processor or the like). FIG. 18 illustrates another embodiment of a wearable device 1700 in the form of a helmet showing a back view. FIG. 19 illustrates a third embodiment of a wearable device 1700 in the form of a helmet with the cable 1706 leading to a wearable garment 1708 (such as a vest or partial vest) that can include a battery or a hub. Alternatively or additionally, the wearable device 1700 can include a crest 1710 or other protrusion for placement of the hub or battery.

Figure 20:
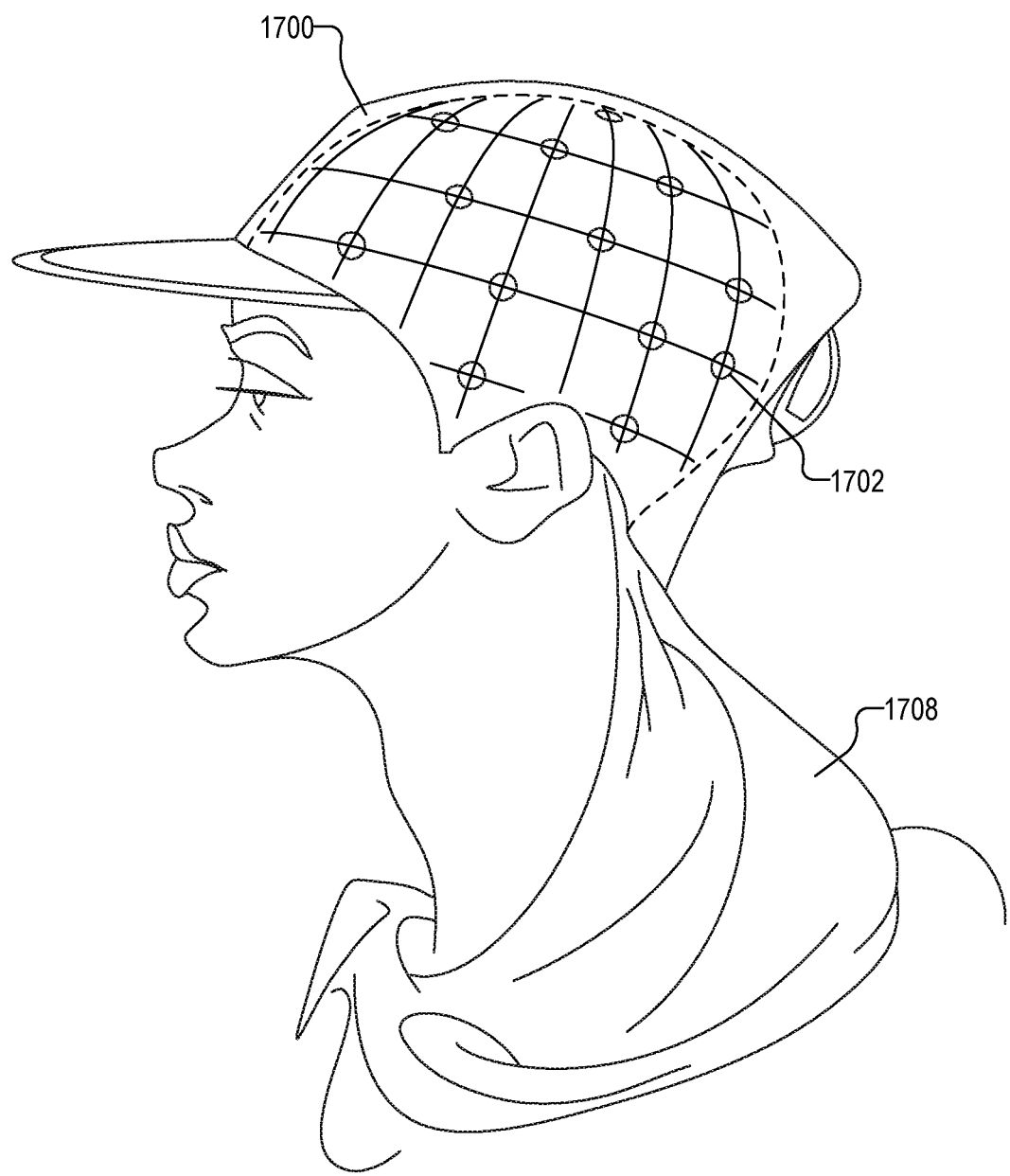
Figure 21:
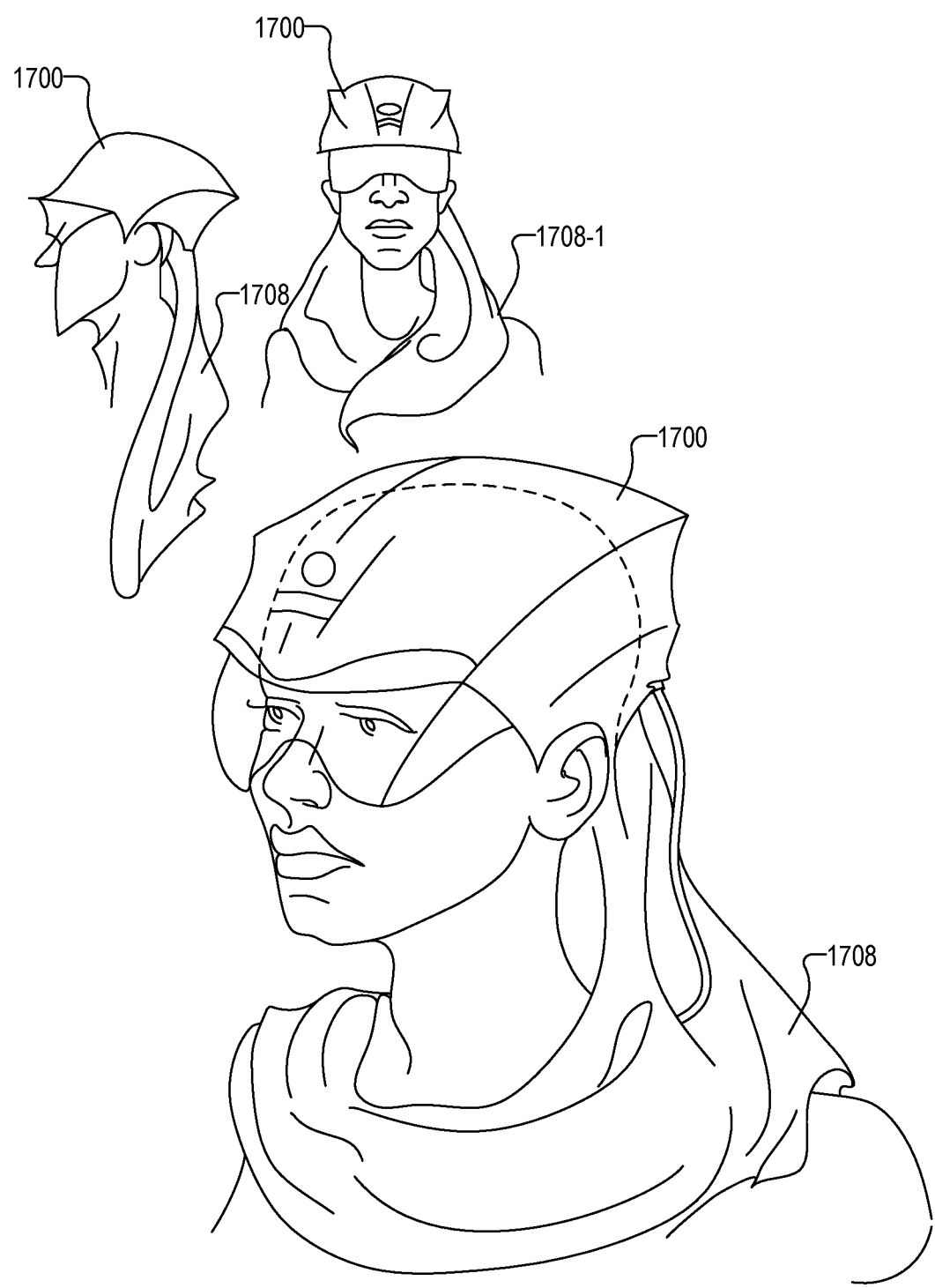
Figure 22:
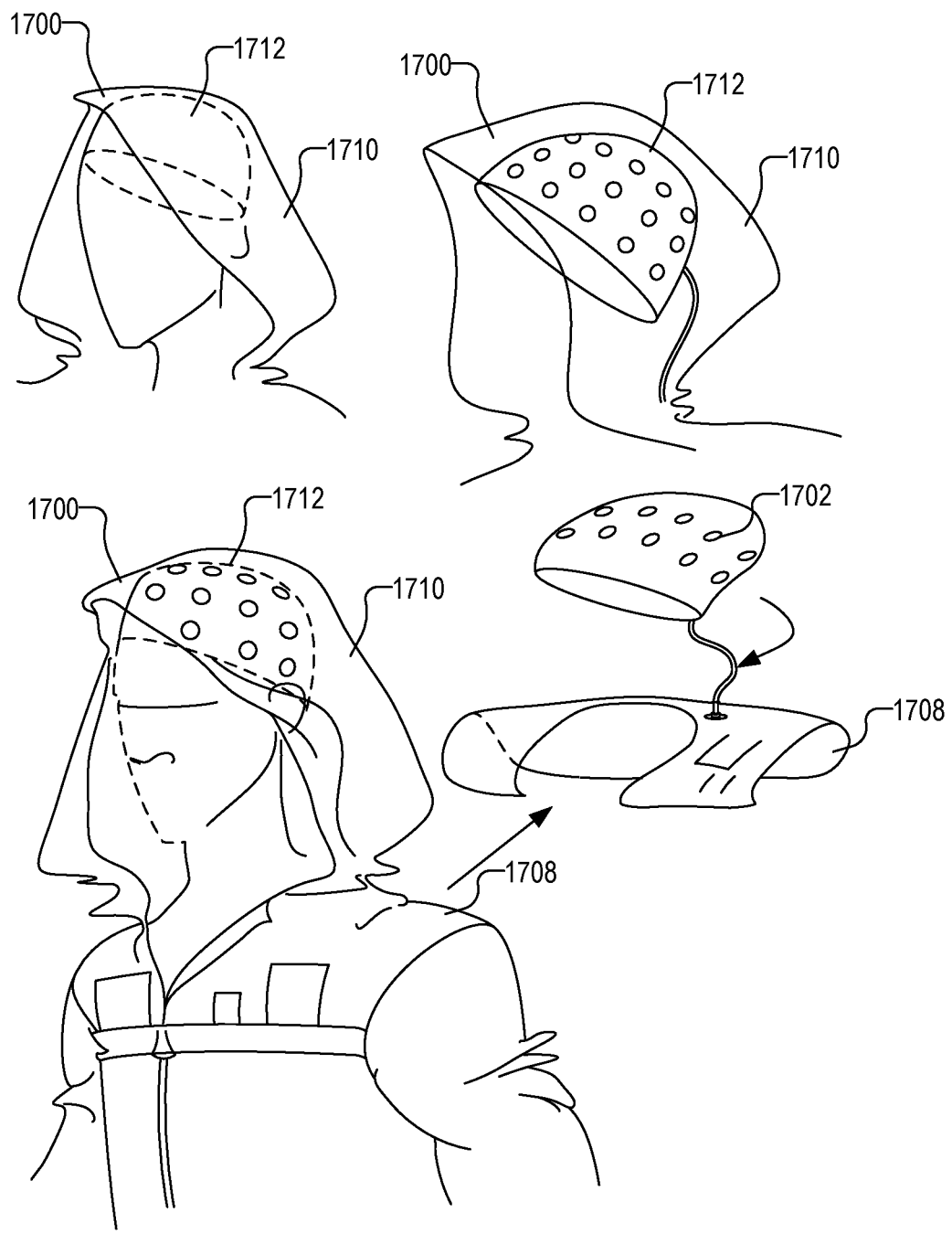

FIG. 20 illustrates another embodiment of a wearable device 1700 in the form of a cap with a wearable garment 1708 in the form of a scarf that may contain or conceal a cable, battery, and/or hub. FIG. 21 illustrates additional embodiments of a wearable device 1700 in the form of a helmet with a one-piece scarf 1708 or two-piece scarf 1708-1. FIG. 22 illustrates an embodiment of a wearable device 1700 that includes a hood 1710 and a beanie 1712 which contains the modules 1702, as well as a wearable garment 1708 that may contain a battery or hub.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 23:
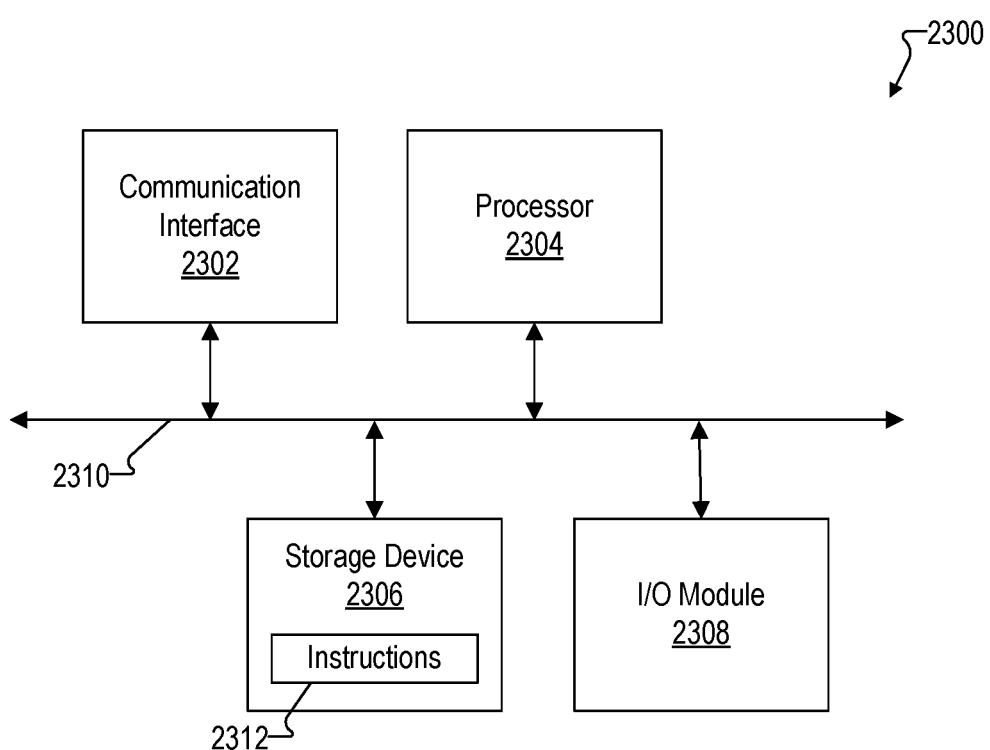
FIG. 23 illustrates an exemplary computing device.

FIG. 23 illustrates an exemplary computing device 2300 that may be specifically configured to perform one or more of the processes described herein. Any of the systems, units, computing devices, and/or other components described herein may be implemented by computing device 2300.

As shown in FIG. 23, computing device 2300 may include a communication interface 2302, a processor 2304, a storage device 2306, and an input/output ("I/O") module 2308 communicatively connected one to another via a communication infrastructure 2310. While an exemplary computing device 2300 is shown in FIG. 23, the components illustrated in FIG. 23 are not intended to be limiting. Additional or alternative components may be used in other embodiments. Components of computing device 2300 shown in FIG. 23 will now be described in additional detail.

Communication interface 2302 may be configured to communicate with one or more computing devices. Examples of communication interface 2302 include, without limitation, a wired network interface (such as a network interface card), a wireless network interface (such as a wireless network interface card), a modem, an audio/video connection, and any other suitable interface.

Processor 2304 generally represents any type or form of processing unit capable of processing data and/or interpreting, executing, and/or directing execution of one or more of the instructions, processes, and/or operations described herein. Processor 2304 may perform operations by executing computer-executable instructions 2312 (e.g., an application, software, code, and/or other executable data instance) stored in storage device 2306.

Storage device 2306 may include one or more data storage media, devices, or configurations and may employ any type, form, and combination of data storage media and/or device. For example, storage device 2306 may include, but is not limited to, any combination of the non-volatile media and/or volatile media described herein. Electronic data, including data described herein, may be temporarily and/or permanently stored in storage device 2306. For example, data representative of computer-executable instructions 2312 configured to direct processor 2304 to perform any of the operations described herein may be stored within storage device 2306. In some examples, data may be arranged in one or more databases residing within storage device 2306.

I/O module 2308 may include one or more I/O modules configured to receive user input and provide user output. I/O module 2308 may include any hardware, firmware, software, or combination thereof supportive of input and output capabilities. For example, I/O module 2308 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 2308 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 2308 is configured to provide graphical data to a display for presentation to a user. The graphical data may be representative of one or more graphical user interfaces and/or any other graphical content as may serve a particular implementation.

Figure 24:
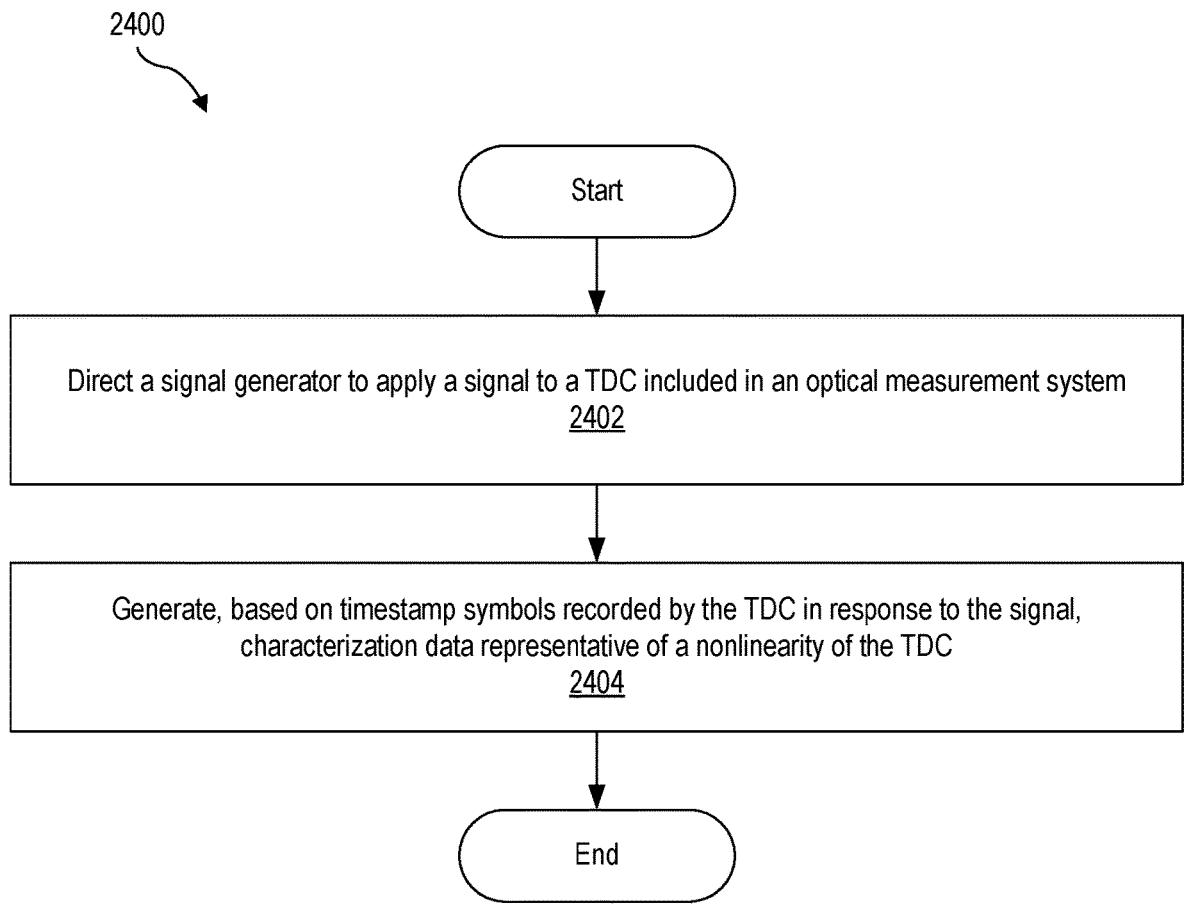
FIGS. 24-25 illustrate exemplary methods.

FIG. 24 illustrates an exemplary method 2400 that may be performed by a processing unit as described herein. While FIG. 24 illustrates exemplary operations according to one embodiment, other embodiments may omit, add to, reorder, and/or modify any of the operations shown in FIG. 24. Each of the operations shown in FIG. 24 may be performed in any of the ways described herein.

In operation 2402, a processing unit directs a signal generator to apply a signal to a TDC included in an optical measurement system.

In operation 2404, the processing unit generates, based on timestamp symbols recorded by the TDC in response to the signal, characterization data representative of a nonlinearity of the TDC.

Figure 25:
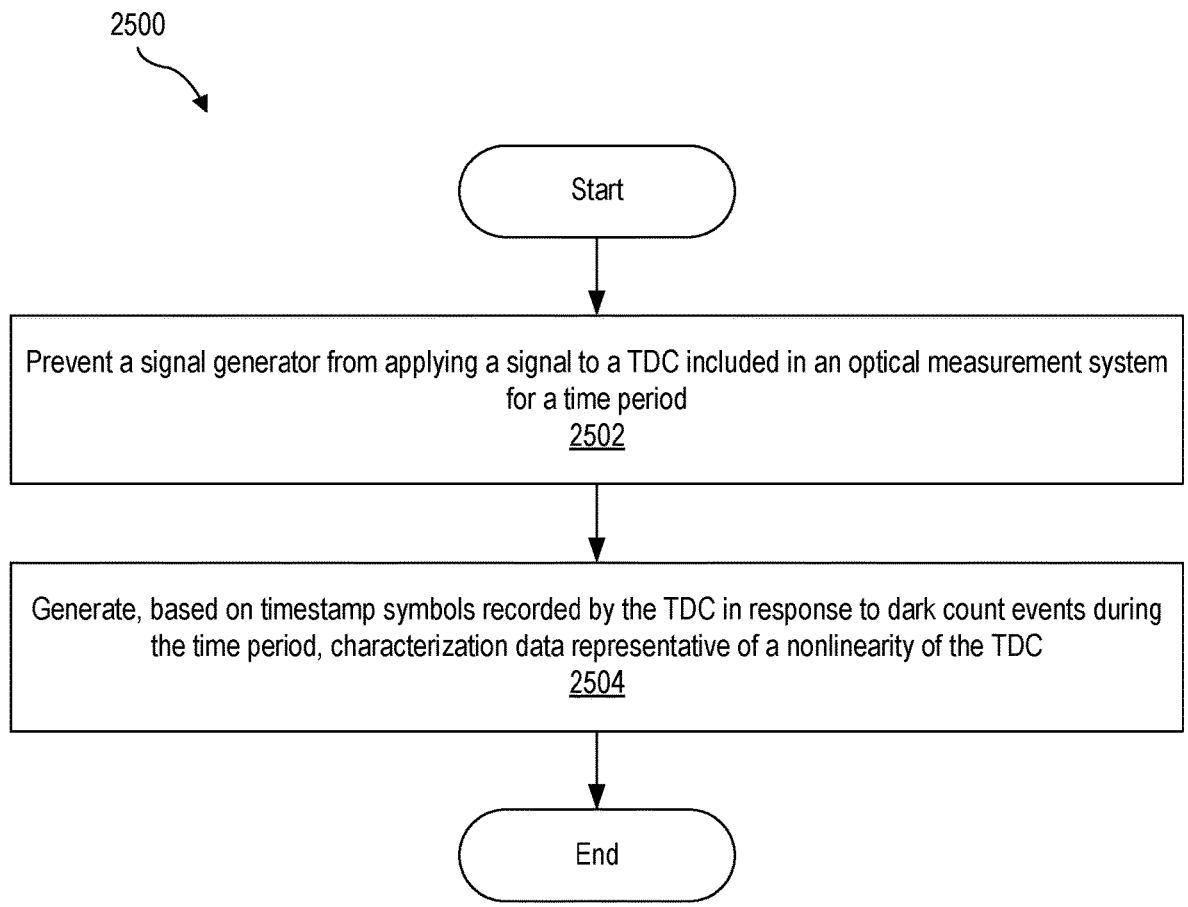

FIG. 25 illustrates an exemplary method 2500 that may be performed by a processing unit as described herein. While FIG. 25 illustrates exemplary operations according to one embodiment, other embodiments may omit, add to, reorder, and/or modify any of the operations shown in FIG. 25. Each of the operations shown in FIG. 25 may be performed in any of the ways described herein.

In operation 2502, a processing unit prevents a signal generator from applying a signal to a TDC included in an optical measurement system for a time period.

In operation 2504, the processing unit generates, based on timestamp symbols recorded by the TDC in response to dark count events during the time period, characterization data representative of a nonlinearity of the TDC.

An illustrative optical measurement system includes a signal generator configured to generate a signal and a processing unit configured to direct the signal generator to apply the signal to a TDC included in the optical measurement system and generate, based on timestamp symbols recorded by the TDC in response to the signal, characterization data representative of a nonlinearity of the TDC.

An illustrative system includes a memory storing instructions and a processor communicatively coupled to the memory and configured to execute the instructions to direct a signal generator to apply a signal to a TDC included in an optical measurement system, and generate, based on timestamp symbols recorded by the TDC in response to the signal, characterization data representative of a nonlinearity of the TDC.

Another illustrative system includes a memory storing instructions and a processor communicatively coupled to the memory and configured to execute the instructions to prevent a signal generator from applying a signal to a TDC included in an optical measurement system for a time period, and generate, based on timestamp symbols recorded by the TDC in response to dark count events during the time period, characterization data representative of a nonlinearity of the TDC.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An optical measurement system comprising:
a signal generator configured to generate a signal; and
a processing unit configured to
direct the signal generator to apply the signal to a time-to-digital converter (TDC) included in the optical measurement system, and
generate, based on timestamp symbols recorded by the TDC in response to the signal, characterization data representative of a nonlinearity of the TDC;
wherein the generating of the characterization data comprises:
generating a histogram of the timestamp symbols recorded by the TDC, the histogram including a plurality of time bins; and
determining a code density metric for each time bin of the histogram, the code density metric representative of a density of timestamp symbols at each time bin of the histogram, the determining the code density metric being performed in accordance with Code density$[i]$=hist_bin$[i]/\Sigma_{all\ bins}$hist_bin$[i]*B_{total}$, where Code density$[i]$ is the code density metric, i is an index for each time bin of the histogram, hist_bin$[i]$ represents a value in the histogram at each time bin i, $B_{total}$ represents a total number of time bins in the histogram, and $\Sigma_{all\ bins}$hist_bin$[i]$ represents a sum of all the values in the histogram.

2. The optical measurement system of claim 1, wherein:
the signal generator comprises a precision timing circuit configured to generate output pulses having either programmable delays or programmable pulse widths, the signal comprising a sequence of the output pulses; and
the directing of the signal generator to apply the signal to the TDC comprises directing the precision timing circuit to sweep the output pulses across either a plurality of delays or a plurality of pulse widths;
wherein the TDC is configured to record the timestamp symbols as the output pulses are swept across the plurality of delays or the plurality of pulse widths.

3. The optical measurement system of claim 2, wherein:
the signal generator further comprises a phase lock loop (PLL) circuit having a PLL feedback period; and
the precision timing circuit is configured to generate the output pulses having programmable delays or programmable pulse widths within the PLL feedback period.

4. The optical measurement system of claim 1, wherein:
the signal generator comprises a light source; and
the signal comprises temporally uniform illumination generated by the light source.

5. The optical measurement system of claim 1, wherein the generating of the characterization data comprises determining, based on the code density metric, a nonlinearity metric for each time bin of the histogram.

6. The optical measurement system of claim 5, wherein the determining of the nonlinearity metric comprises normalizing the code density metric.

7. The optical measurement system of claim 1, wherein the processing unit is further configured to normalize a transfer function of the TDC in accordance with $$\text{hist\_bin\_norm}[i] = \frac{\text{hist\_bin}[i]}{\text{code density}[i]},$$

where hist_bin_norm$[i]$ represents the normalized transfer function.

8. The optical measurement system of claim 1, wherein the processing unit is further configured to perform, based on the characterization data, an action associated with the TDC.

9. The optical measurement system of claim 8, wherein the performing of the action comprises normalizing, based on the characterization data, a transfer function of the TDC.

10. The optical measurement system of claim 8, wherein the performing of the action comprises rating the TDC based on the characterization data.

11. The optical measurement system of claim 1, wherein:
the TDC is included in an array of TDCs; and
the processing unit is configured to disable other TDCs within the array of TDCs while the signal is being applied to the TDC.

12. The optical measurement system of claim 1, further comprising a multiplexer configured to selectively pass, to the TDC, the signal or a photodetector output pulse generated by a photodetector associated with the TDC.

13. The optical measurement system of claim 12, wherein the processing unit is configured to direct the multiplexer to pass the signal to the TDC.

14. The optical measurement system of claim 1, further comprising storing the characterization data within a memory of the optical measurement system.

15. The optical measurement system of claim 1, wherein the generating of the characterization data is performed in response to an event occurring within the optical measurement system.

16. The optical measurement system of claim 15, wherein the event comprises a startup of the optical measurement system.

17. The optical measurement system of claim 1, wherein:
the processing unit is configured to place the optical measurement system in a calibration mode; and
the directing and generating are performed while the optical measurement system is in the calibration mode.

18. The optical measurement system of claim 1, further comprising a wearable assembly configured to be worn by a user, wherein one or more of the signal generator or the processing unit are included in the wearable assembly.

* * * * *